(12) United States Patent
Perelman

(10) Patent No.: US 9,788,728 B2
(45) Date of Patent: Oct. 17, 2017

(54) ENDOSCOPIC POLARIZED MULTISPECTRAL LIGHT SCATTERING SCANNING METHOD

(75) Inventor: Lev T. Perelman, Brookline, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 1395 days.

(21) Appl. No.: 13/145,851

(22) PCT Filed: Jan. 22, 2010

(86) PCT No.: PCT/US2010/000166
§ 371 (c)(1),
(2), (4) Date: Nov. 2, 2011

(87) PCT Pub. No.: WO2010/085348
PCT Pub. Date: Jul. 29, 2010

(65) Prior Publication Data
US 2012/0041290 A1    Feb. 16, 2012

Related U.S. Application Data

(60) Provisional application No. 61/147,074, filed on Jan. 23, 2009.

(51) Int. Cl.
*A61B 6/00*    (2006.01)
*A61B 5/00*    (2006.01)

(52) U.S. Cl.
CPC .......... *A61B 5/0062* (2013.01); *A61B 5/0071* (2013.01); *A61B 5/0075* (2013.01); *A61B 5/0084* (2013.01); *A61B 5/0066* (2013.01)

(58) Field of Classification Search
CPC ... A61B 5/0062; A61B 5/0071; A61B 5/0075; A61B 5/0084
See application file for complete search history.

(56) References Cited

U.S. PATENT DOCUMENTS 5,048,524 A * 9/1991 Bailey ........................... 600/327
6,091,984 A * 7/2000 Perelman et al. ............ 600/476
(Continued)

FOREIGN PATENT DOCUMENTS

WO    WO 0042912     7/2000
WO    WO 03059150    7/2003

OTHER PUBLICATIONS

Muller et al, Spectroscopic Detection and Evaluation of Morphologic and Biochemical Changes in Early Human Oral Carcinoma, Cancer, vol. 97, Issue 7, Mar. 2003, pp. 1681-1692.*
(Continued)

*Primary Examiner* — James Kish
(74) *Attorney, Agent, or Firm* — Wolf, Greenfield & Sacks, P.C.

(57) ABSTRACT

Method and system for early detection of precancerous and other abnormal changes in tissue of various organs. The system comprises a combination of endoscopic scanning with light scattering spectroscopy and improves detection of abnormalities that may otherwise remain undetected. The system may include a probe that collects data of quality that is independent of a distance of the probe from the scanned tissue. During endoscopy, tissue of an organ is imaged using polarized multispectral light scattering scanning and results are presented to a user in a manner that allows detecting abnormal morphological and biochemical changes in the tissue. A determination of whether to perform biopsy may be performed while the endoscopy is being performed, which thus provides guided biopsy. An entire surface of the organ may be rapidly scanned and results of the scanning are analyzed with a reduced time delay.

27 Claims, 24 Drawing Sheets

(56) References Cited

U.S. PATENT DOCUMENTS

| | | | |
|---|---|---|---|
| 6,404,497 B1* | 6/2002 | Backman | A61B 5/0084 356/369 |
| 6,485,413 B1 | 11/2002 | Boppart et al. | |
| 2001/0056237 A1* | 12/2001 | Cane | A61B 5/0059 600/475 |
| 2002/0101566 A1* | 8/2002 | Elsner | G01N 21/4795 351/200 |
| 2003/0040668 A1* | 2/2003 | Kaneko | A61B 1/00096 600/407 |
| 2003/0167007 A1* | 9/2003 | Belson | 600/473 |
| 2005/0094147 A1* | 5/2005 | Yaroslavsky et al. | 356/417 |
| 2007/0274650 A1* | 11/2007 | Tearney et al. | 385/118 |
| 2008/0021275 A1* | 1/2008 | Tearney et al. | 600/115 |
| 2008/0039720 A1* | 2/2008 | Balas | 600/431 |
| 2008/0267472 A1 | 10/2008 | Demos | |
| 2010/0056927 A1* | 3/2010 | Van Gogh et al. | 600/476 |

OTHER PUBLICATIONS

International Search Report dated May 7, 2010 from corresponding International Application No. PCT/US2010/000166.

\* cited by examiner

ENDOSCOPIC POLARIZED MULTISPECTRAL LIGHT SCATTERING SCANNING METHOD

RELATED APPLICATIONS

This application claims the benefit under 35 U.S.C. §119 (e) of U.S. provisional application 61/147,074, filed Jan. 23, 2009, entitled "POLARIZED LSS ENDOSCOPIC SCANNING INSTRUMENT," the content of which is incorporated herein in its entirety.

STATEMENT REGARDING FEDERALLY SPONSORED RESEARCH OR DEVELOPMENT

This invention was made with government support under grant number EB003472 awarded by NIH. The government has certain rights in the invention.

FIELD OF THE INVENTION

The present invention relates to imaging tissue of an organ using polarized multispectral light scattering scanning method to detect abnormal morphological and biochemical changes indicative of precancerous dysplasia or other tissue abnormalities.

BACKGROUND

Early detection of precancerous changes in various organs in the human body may improve results of treatment and ultimately save lives. Techniques used to detect such changes include visual endoscopy and collection of tissue samples (i.e., biopsy) at predetermined sites that are typically used to analyze tissue of organs for abnoinial changes.

As an example, tissue of the esophagus may be examined using light scattering spectroscopy. Esophageal adenocarcinoma is a form of cancer the incidence of which is increasing rapidly in the United States. Almost 100% of cases of esophageal adenocarcinoma occur in patients with Barrett's Esophagus (BE), an otherwise benign condition in which metaplastic columnar epithelium replaces the normal squamous epithelium of the esophagus.

Although the prognosis of patients diagnosed with adenocarcinoma may be poor, the chances of successful treatment increase significantly if the disease is detected at the dysplastic stage. Once BE has been identified in a patient, the patient may be enrolled in an endoscopy/biopsy surveillance program, presuming that the patient is a candidate for surgery should high-grade dysplasia be detected. The surveillance of patients with BE for dysplasia may be challenging in at least three respects. First, dysplasia may not be visible during routine endoscopy. Thus, known testing techniques often require that numerous biopsy specimens be taken at random locations along the patient's esophagus for histopathologic examination of the excised tissue. Second, the histopathologic diagnosis of dysplasia is problematic because there is poor interobserver agreement on the classification of a particular specimen, even among expert gastrointestinal pathologists. Third, reliance on the histopathologic examination imposes a time delay between endoscopy and diagnosis, which may severely limit the diagnostic accuracy of the endoscopic procedure.

SUMMARY OF INVENTION

Applicants have appreciated that techniques of detecting changes in tissue of an organ may be improved by employing multispectral light scattering scanning method together with endoscopy. The multispectral light scattering scanning may be used to collect data on one or to more portions, or sites, of the organ and use the data to determine whether there are any changes in the tissue of the organ that may be indicative of a precancerous or other abnormal condition. In some embodiments, polarized multispectral light scattering scanning method is employed.

Embodiments of the invention provide a method that may be used to perform rapid optical scanning and multispectral imaging of the entire surface of the organ. Both internal and external surface of the organ may be scanned. The analysis of the data collected while scanning the surface of the organ may allow detecting otherwise invisible changes one or more portions of the organ affected by a certain degree of dysplasia. Thus, suspicious sites where a biopsy is desired to be taken for further analysis may be identified. Accordingly, the method may be used to guide the biopsy and sample of the tissue may be collected from the suspicious sites while the scanning is being performed.

Embodiments of the invention may enable fast and reliable spectroscopic detection and diagnosis of dysplasia in patients with BE during endoscopy. Exemplary embodiments may provide an instrument and method for safely, quickly, and reliably surveying the entire length of Barrett's esophagus for endoscopically invisible dysplasia, thereby avoiding harms and risks associated with random biopsy surveillance.

According to one aspect of the present invention, an instrument, method and system for examination of internal tissue using polarized light scattering spectroscopy (PLSS) is described. In one embodiment, an instrument is described that can be used to detect various conditions in esophageal tissue including, but not limited to: Barrett's esophagus (BE), low-grade dysplasia (LGD), high-grade dysplasia (HGD), and/or adenocarcinoma. The described instrument may be able to distinguish between various tissue conditions. The instrument may be used to examine gastrointestinal tissue in vivo and/or ex vivo.

In some embodiments, the instrument may permit non-contact scanning over regions of gastrointestinal tissue. The described instrument may be used to obtain data at spatially separated tissue locations, along a line and/or over a two-dimensional area, as the invention is not limited in this respect.

In one embodiment, an instrument includes a light scattering spectroscopy (LSS) probe configured to be inserted into the gastrointestinal tract of a patient. The probe includes illumination optics for illuminating tissue, and receiving optics for receiving light scattered by the tissue to be directed to one or more spectrometers. The illumination optics may be configured for illuminating tissue with collimated light and the receiving optics may be configured to collimate received light. A portion of the received light with a certain angular distribution may be collected. The probe may also include a polarizer for polarizing light scattered by the tissue. The probe may include a scanning assembly configured to move at least some of the illumination optics with respect to a non-scanning portion of the probe/and or with respect to a gastroscope. At least some of the illumination optics may rotate, tilt, pivot and/or translate with respect to the non-scanning portion of the probe and/or the gastroscope.

In one embodiment, an LSS instrument includes an LSS probe and one or more spectrometers for generating a spectrum of scattered light received by probe. The instrument may further include a control unit for controlling a direction of the illuminating beam from the polarizer. The control unit may interact with a scanning assembly of the probe to scan illuminating and/or receiving optics of the LSS probe.

According to another aspect of the invention, a method and system for obtaining diagnostic information from polarized LSS data of tissue is provided. The described method may be used to provide diagnostic information corresponding to separate tissue locations, corresponding to tissue located along a line and/or corresponding to tissue over a two-dimensional area, as the invention is not limited in this respect. The described system may be used to analyze spectral data obtained from one or more tissue locations in vivo or from tissue samples ex vivo to produce data indicating a diagnostic condition at each tissue location. The described system may be used to obtain a real-time map of a diagnostic condition over an area of tissue during an endoscopy. Thus, an entire surface of the organ may be rapidly scanned and results of the scanning are analyzed with a reduced time delay. The system may also include an imaging system for providing an image of the tissue during an endoscopy. The system may enable biopsies at locations where a certain tissue condition has been identified or is suspected based on a map of nuclear tissue structure and/or a map of a diagnostic condition obtained by LSS. A map of nuclear tissue structure and/or a map of a diagnostic condition may be displayed along with an image of the same location during an endoscopy.

In one embodiment, a method is described that can be used to identify a tissue condition at various tissue locations during a procedure before a probe is removed from a patient. The described method may include providing information regarding a diagnostic condition over a two-dimensional area based on data obtained from an in vivo LSS instrument. The method may further include providing a two-dimensional map of a diagnostic condition and two dimensional image of an area of tissue.

Some embodiments of the invention provide a system for obtaining characteristics of tissue of an organ. The system may comprise a device such as a probe configured to scan the tissue of the organ, which may comprise an illumination optics system configured to illuminate at least one portion of the tissue of the organ with collimated light and a receiving system configured to receive light backscattered by at least one portion as a result of the illumination. The system may also comprise at least one spectrometer configured to generate at least one spectrum from the received light, an imaging unit configured to obtain at least one image of the at least one portion, an analysis unit configured to analyze the at least one spectrum to provide at least one characteristic of the at least one portion, and a user interface configured to present to a user information comprising the at least one image in association with at least one visual representation of the at least one characteristic, wherein the information is used to determine whether to take a tissue sample from the at least one portion.

BRIEF DESCRIPTION OF DRAWINGS

In the figures, each identical or nearly identical component that is illustrated in various figures is represented by a single reference character. For purposes of clarity, not every component is labeled in every figure, nor is every component of each embodiment or aspect of the invention shown where illustration is not necessary to allow those of ordinary skill in the art to understand the invention.

For purposes of clarity, not every component may be labeled in every drawing. In the drawings.

DETAILED DESCRIPTION

Figure 1:
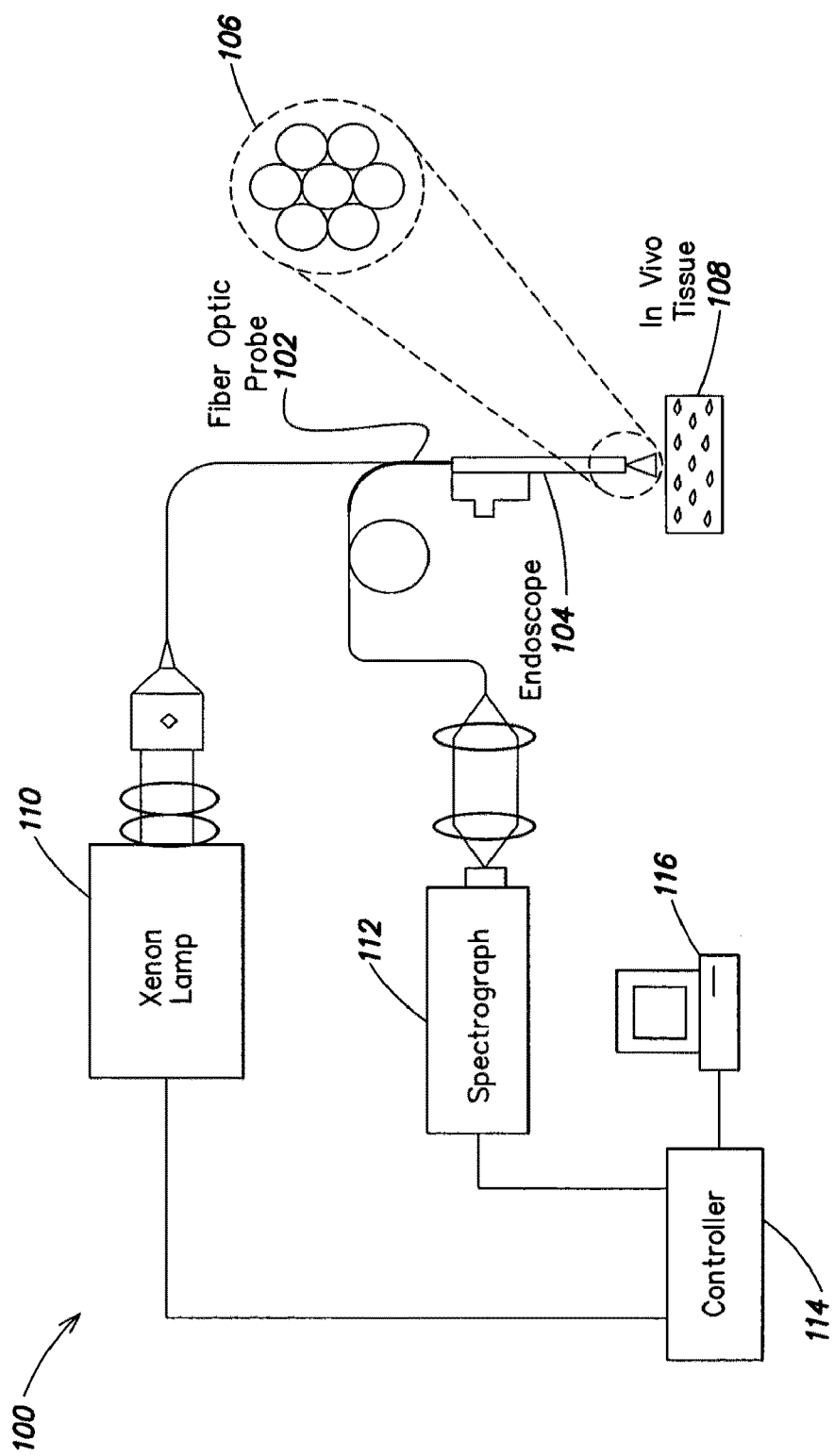
FIG. 1 is a schematic diagram of the proof-of-principle system used to perform LSS, in accordance with some embodiments of the invention.

Embodiments of the invention provide a system and a method of detecting abnormal changes in tissues of organs using a combination of light scattering spectroscopy (LSS) with endoscopy. Employing a probe for performing the light scattering spectroscopy with either existing or specifically designed endoscopic devices results in improved detection of abnormalities in the tissues of organs that may otherwise remain undetected. In particular, this technique may improve early detection of certain morphological and histological changes which, albeit being potentially precancerous, may be amenable to treatments if detected early. Thus, lives of many patients may potentially be saved.

Some embodiments of the invention provide techniques for early detection of changes in the tissue of the esophagus that may be initial stages of the esophageal adenocarcinoma. Thus, in accordance with one aspect of the present invention, instruments, systems and methods for examining a portion of the gastrointestinal tract of a patient that is suspected to have Barrett's Esophagus (BE) using LSS are provided. However, embodiments of the invention are not limited to esophagus of any other organ of the gastrointestinal tract and may be applied to detection of abnormal changes is various organs of reproductive tract, respiratory tract and other systems.

A system in accordance with some embodiments of the invention may comprise an exemplary instrument that may use non-contact LSS to obtain information about a tissue condition in a patient's esophagus in vivo. The instrument may comprise illumination optics used for illuminating a portion, or a site, of the surface of the esophagus with one or more polarized light beams and receiving optics for receiving reflected light beams that result from backscattering of the incident polarized light beams from the surface of the illuminated site. In some embodiments, the instrument may include optics for collimating the incident polarized light beams and receiving optics for collimating the received light. Further, the instrument may include a probe with illuminating optics and/or receiving optics that may be moveable relative to a stationary portion of the probe, for scanning a line along tissue or for scanning an area of tissue.

The probe may be inserted into or otherwise associated with the instrument such as an endoscope. The probe and the illumination and receiving optics of the probe, in combination with an analysis technique developed to process data collected by the probe, may allow rapid scanning of a organ. It should be appreciated that embodiments of the invention are not limited to any particular probe and any suitable device may be substituted. Accordingly, large portions of the organ such as the esophagus may be scanned, which makes the method and system in accordance with the embodiments of the invention applicable in a clinical setting. Indeed, Applicants demonstrated that a system employing polarized LSS in accordance with some the embodiments of the invention provides reliable detection of precancerous changes in the esophagus, as discussed in more detail below. In some embodiments of the invention, two-dimensional scanning of the tissue may be performed. The instrument may be insensitive to a spacing between a probe tip and the tissue being examined. As a result, a quality of the detection may not be affected by peristaltic movements of organs of the gastrointestinal tract.

Some embodiments of the invention provide a system in which polarized light scattering spectroscopy is employed in combination a suitable endoscopic device. Thus, a polarized light scattering spectroscopy (PLSS) endoscopic instrument system may be employed. The PLSS may be defined as an optical technique that relates the spectroscopic properties of light elastically scattered by light scattering particles such as, for example, epithelial cell nuclei to their size, shape and refractive index.

To be suitable for use by a medical practitioner in a clinical setting, measurements collected using a EPSS device, or instrument, from a potion of the tissue in accordance with some embodiments of the invention, need to be easily interpreted as reliably indicative of certain conditions of the tissue. This description focuses, as an example, on screening the esophagus of patients with BE for presence of dysplasia of different degree and, possibly, carcinoma. If precancerous changes in the esophagus of such patient are detected early enough, chances of the patient's survival increase significantly. However, it should be appreciated that embodiments of the invention are not limited to detecting abnormal changes in tissue of the esophagus and the detection may be performed in tissue of various other organs from gastrointestinal tract, as well as various organs from reproductive, respiratory and other tracts.

Accordingly, Applicants have developed an analysis technique that allows extracting information on the underlying structure of the examined tissue from light diffusely scattered from the tissue (which comprises both transmitted light and backscattered light). The information may comprise any suitable characteristics describing morphological and histological properties of tissue of the esophagus or any other organ. For example, the characteristics providing information about nuclear enlargement, crowding and hyperchromaticity may comprise epithelial nuclear size, nuclear size distribution, and chromatin density, respectively. Also, the characteristics may comprise information on the density of the collagen matrix, hemoglobin concentration and oxygen saturation of hemoglobin in the underlying tissue.

Further, the structural information on a certain site on the tissue may be mapped to a location of the site. The mapping may be presented to a user in any suitable format that allows the user to visually determine sites that may exhibit abnormal changes. As a result, better diagnosis may be possible. In some embodiments, the mapping may be presented to the user in real time—in response to illuminating the site, and collecting and processing the results during the endoscopy of the patient.

To provide the visual representation of the examined portion of the tissue as discussed above, in some embodiments of the invention, during endoscopic scanning of the surface of an organ such as the esophagus using the LSS probe (e.g., PLSS probe), images of the surface may simultaneously be taken. The images may be taken using any suitable device. As a result, information from the images may be combined with information provided by an analysis of data collected by the probe. In one embodiment, image information may be overlaid with a color-coded map, which may be semitransparent, representing diagnostic information derived using LSS. The imaging provides improved visual representation of the examined tissue and may thus lead to a more accurate diagnosis.

Applicants have developed a model for assessing the esophagus and demonstrated modeling clinical tissue reflectance in terms of the underlying tissue constituents such as scatterers and absorbers. In accordance with some embodiments of the invention, Applicants have created an analytical model, using the diffusion approximation, to describe the tissue reflectance spectrum collected by a finite sized probe with a certain effective radius.

Applicants' analysis indicates that the scattering coefficient of tissue decreases significantly during the development of dysplasia, suggesting that changes that are not observed histopathologically are taking place within the lamina propria and submucosa before the onset of invasion. The lamina propria is a layer of loose connective tissue which lies beneath the epithelium and together with the epithelium constitutes the mucosa. In the gastrointestinal tract, the submucosa is the layer of dense irregular connective tissue that supports the mucosa, as well as joins the mucosa to the bulk of underlying tissue such as smooth muscle.

In some embodiments, a EPSS instrument employs collimated illumination and collection optics that enable the instrument to collect data for generating maps of epithelial tissue that may not be affected by the distance between a probe tip of the instrument and the mucosal surface. This may make the instrument less sensitive to peristaltic motion.

The system employing the PLSS may include, among any other suitable components, a computer programmed to produce structural tissue information or information regarding a tissue condition from in vivo spectroscopic data. The system may include any suitable display device for displaying information on the structure of the tissue and information that relates the structure to a corresponding diagnostic condition. For example, the system may include a display device for displaying a map of structural tissue information or a map of a tissue condition over an area. Accordingly, the system may enable in vivo detection and diagnosis of dysplastic tissue and/or adenocarcinoma during endoscopy for patients with Barrett's Esophagus. It should be appreciated that embodiments of the invention allow detecting dysplasia and other precancerous changes in tissues of other organs such as the lungs, colon, kidney, pancreas, urinary bladder, uterus, gall bladder, intestine and others.

Embodiments of the invention provide a method may be used to perform rapid optical scanning and multispectral imaging of the entire surface of the organ. The analysis of the data collected while scanning the surface of the organ may allow detecting otherwise invisible changes one or more portions of the organ affected by a certain degree of dysplasia. Thus, suspicious sites where a biopsy is desired to be taken for further analysis may be identified. Accordingly, the method may be used to guide the biopsy and a sample of the tissue may be collected from the suspicious sites while the scanning is being performed.

An embodiment of the invention describes EPSS instrument that provides a diagnostic screening tool that may enable a gastroenterologist to rapidly survey the region of Barrett's esophagus (BE) in a patient with this disease, and allow the gastroenterologist to determine with high probability and in real-time, regions of dysplasia and carcinoma. The instrument may distinguish between the categories of adenocarcinoma, high-grade dysplasia, low-grade dysplasia, indefinite for dysplasia and non-dysplastic BE. It may be able to perform measurements of the full length of the esophagus in about two minutes and provide the information in real time. Suspicious areas can then be biopsied and the diagnosis verified. The instrument may reduce the need for performing either systematic or random biopsies for screenings or surveillance. Thus, it may provide a powerful tool for screening the large population of Barrett's esophagus patients for early precancerous changes.

An exemplary EPSS instrument may be based on the technique of light scattering spectroscopy (LSS), which has been demonstrated in a proof-of-principle study to be able to perform such measurements in the epithelial tissue of five different organs, including BE where these proof-of-principle studies were the most extensive and successful. The proposed technique may greatly reduce the time and labor involved in performing screening and obtaining diagnoses, cause less patient discomfort, require fewer biopsies, and help the pathologist to base a diagnosis on uniform quantitative criteria, making the diagnosis more consistent. Because of these advantages, embodiments of the invention may significantly improve the probability of detecting potential malignancies in the early stages, when cures are possible, and it may be highly cost effective.

Applicants have demonstrated that the developed system and method for detection of dysplasia in Barrett's esophagus provided by some embodiments of the invention are clinically useful. The system which may be referred to as endoscopic polarized scanning spectroscopy (EPSS) allows to rapidly survey a comparatively large area of the esophagus while simultaneously detecting changes on a cellular scale. This system comprises a combination of a scanning instrument that is suitable for use in endoscopy with a unit for polarized light scattering spectroscopy (PLSS). To assess performance of the EPSS system, Applicants have performed experiments in humans using the system, which is discussed in more detail below.

Not all patients with BE progress to adenocarcinoma. Some live their entire lives without undergoing malignant or neoplastic transformation. Others demonstrate a rapid progression to carcinoma, and will die of esophageal cancer if it is not diagnosed and treated in a timely manner. The standard of care for surveillance of patients with BE is still developing. Although periodic endoscopic surveillance of patients with Barrett's esophagus has been shown to detect carcinoma in its earlier stages, random biopsy surveillance has significant limitations. Dysplastic and early carcinomatous lesions arising in Barrett's esophagus are not visible macroscopically; therefore, surveillance may require extensive random biopsies of the esophagus and histologic examination of the excised tissue for dysplasia. Taking biopsy specimens at random locations for surveillance may be prone to sampling error (missed dysplastic lesions) and may have significant cost and risk. There also is significant interobserver disagreement between pathologists in diagnosing dysplasia. Large sampling error, significant cost and risk, and disagreement between pathologists in diagnosing dysplasia in specimens limit the value of the current random biopsy endoscopic surveillance strategy.

Similarly, there is little agreement on the most appropriate management of HGD when it is found. Because of the marked variability (range 0-73%; most often quoted as 33%) in finding unsuspected carcinoma in patients with HGD, esophagectomy (surgical removal of part or all of the esophagus) is recommended by many clinicians to eliminate the risk of carcinoma or to detect and treat it at an early and treatable stage. However, this approach has been criticized because of the high morbidity and mortality associated with esophagectomy, the lack of a systematic biopsy protocol prior to surgery, and the variable natural history of the disease.

Dysplasia in the gastrointestinal tract is defined as neoplastic epithelium confined within an intact basement membrane. Dysplasia in BE can be classified as low or high-grade, based on criteria originally defined for dysplasia in inflammatory bowel disease. Low-grade dysplasia (LGD) is defined primarily by cytological abnormalities, including nuclear enlargement, crowding, stratification, hyperchromasia, mucin depletion and mitoses in the upper portions of the crypts. These abnormalities extend to the mucosal surface. High-grade dysplasia (HGD) is characterized by even more pronounced cytological abnormalities, as well as glandular architectural abnormalities including villiform configuration of the surface, branching and lateral budding of the crypts, and formation of the so-called back-to-back glands. When there is any doubt as to the significance of histological abnormalities in a specimen because of inflammation, ulceration or histological processing artifacts, the findings may be classified as indefinite for dysplasia (IND) in order to prevent unnecessary clinical consequences.

Optical techniques that have been explored for detecting dysplasia in BE include light scattering spectroscopy (LSS), diffuse reflectance spectroscopy, laser-induced fluorescence (LIF) spectroscopy, Raman spectroscopy and optical coherence tomography (OCT). These techniques have been explored for significantly enhancing the probability of detecting dysplasia during an endoscopy and potentially reducing harm from random biopsy surveillance by distinguishing between dysplastic and non-dysplastic tissue in vivo.

Laser Induced Fluorescence (LIF) spectroscopy during endoscopy is believed to measure the abnormal concentrations of certain endogenous fluorophores such as porphyrins in dysplastic and malignant tissue. LIF using tissue autofluresence has shown some promise for the detection of HGD. However, diagnostic algorithms for analysis of the LIF data from tissue autofluoresence have not been able to correctly classify sites with LGD and focal HGD. Other fluorescence spectroscopy studies using exogenous fluorophores have also reported some positive results for detecting high-grade dysplasia. However, focal high-grade and low-grade lesions have not been detected reliably using this technique.

Raman spectroscopy is based on changes induced by light in the vibrational and rotational states of molecular bonds. Raman scattering can occur in response to a wide range of wavelengths, including visible, UV, and near-infrared. Because most biologic molecules are Raman-active, Raman spectroscopy could potentially be used to determine the biochemical status of tissues. Unfortunately, the intensity of a Raman emission spectrum is extremely low, typically a million times weaker than the background fluorescence that results when tissue is excited by ultraviolet and visible wavelengths of light. Thus, Raman spectra are normally obscured by a broad band of fluorescence when light in the visible range is used to excite tissue.

Despite these limitations, a Raman spectroscopy system has been used in vivo in gastrointestinal endoscopy. Raman spectra were obtained in 5 seconds with a low signal-to-noise ratio. However, analysis of the acquired data revealed only small differences between normal and diseased tissues and indicated the need for a system and analysis algorithm that more clearly distinguishes between normal and diseased tissue.

Optical coherence Tomography (OCT) provides two-dimensional cross-sectional images of the gastrointestinal tract of a patient. Like endoscopic ultrasound, OCT provides true anatomic images corresponding to the layers of the gastrointestinal tract (e.g. mucosa, submucosa, muscularis propria, and serosa/adventitia). However, by using light instead of ultrasound waves, the resolution of OCT is nearly 10-fold greater than that of high frequency endoscopic ultrasound, and approaches that of light microscopy. Preliminary reports concerning OCT in patients with BE indicate that Barrett's and normal squamous epithelium can be readily differentiated by OCT. However, because the most characteristic changes in malignant transformation of BE are happening on the cellular and sub-cellular scale, resolution of OCT is not sufficient yet to observe those changes. Whether OCT might be used to detect early-stage cancer or HGD in the future is uncertain.

Although the above results indicate the diagnostic potential of LIF, and Raman spectroscopy and OCT, further improvements in accuracy and methodology may be needed to provide useful clinical tools. Most of the diagnostic algorithms employed have used only simple diagnostic indices, such as intensity ratios, although a few have employed full spectral methods. Further, none of these methods permits direct interpretation of changes in tissue structure and composition from obtained data. Diagnostic correlations have been largely empirical. A major limitation of the techniques reviewed in this section may be the current inability to detect changes in tissue on cellular and sub-cellular scale, the level on which many structural changes due to dysplasia occur.

For example, precancerous changes in the mucosae of various organs including the esophagus share common histological and cytological features. These features manifest themselves as morphological and biochemical alterations that are mainly confined to cellular epithelial layer. To detect those features a technique is needed, which would target microscopic properties of cells and subcellular organelles. Light scattering is sensitive to those changes. Promising results cited herein and discussed below demonstrate that LSS can provide such information in BE.

Before embodiments of the invention including methods instruments and systems are described in detail with respect to FIGS. 7 through 15D, an explanation is provided of how data obtained from polarized light scattering spectroscopy relates to structural information of cells in tissue.

Light Scattering Techniques for Tissue Characterization

Although single scattering of collimated light has been used to study cells and subcellular structures in suspension, this approach cannot be directly used in tissue, because light incident on tissue is randomized by multiple scattering.

Nevertheless, diffusely scattered light from tissue (both transmitted light and backscattered light) contains information about the tissue's underlying structure. However, because of randomization, the information in diffusely scattered light from tissue is averaged over several transport lengths. On the other hand, light scattering in the thin layer at the epithelial tissue surface is not completely randomized, and information about individual scatterers in this layer can be retained, even if the layer thickness is significantly smaller than a transport length.

Different studies have demonstrated a relationship between light scattering, tissue structure and a tissue condition, as described below. In measurements of reduced scattering and absorption coefficients of liver tissue, most of the scattering has been attributed to mitochondrial content of the hepatocytes. In measurements of the variation in the refractive index of fibroblasts, evidence was found of a broad distribution of scatterers ranging from 2 to 0.2 µm. It has been shown that refractive indices of the cell nucleus and membranes are significantly higher than those of other subcellular structures and that nuclei provide the main contribution to forward scattering in lymphocytes. It has also been shown that the nucleus scatters predominantly in the forward direction, while smaller particles scatter at larger angles. Scattering studies on cell suspensions have shown that scattering takes place at the structures within the cells rather than from the cell surface. Most of these studies were carried out on cell suspensions. Recently, polarized backscattering from tissue was used to obtain images of biological cell suspensions. It was shown that in fibroblasts, mitochondria are the strongest scatterers. Differences in mitochondria size and concentration were observed between healthy and diseased cells and tissues.

Applicants have developed a new method of tissue analysis and diagnosis based on LSS and applied it to detection of dysplasia in BE. Applicants collected and analyzed clinical spectra to extract tissue characteristics related to the underlying optical parameters of the epithelial cells in BE. These tissue characteristics may include the size distribution of epithelial cell nuclei and nuclear density. Unlike simple diagnostic indices, these characteristics contain information about the disease state of the tissue. These characteristics may provide better diagnostic indices, because they contain more information regarding the tissue, and also because they permit direct interpretation of tissue composition.

Results with a Single Point Probe

The ability of LSS to distinguish various stages of dysplasia in patients with BE has been demonstrated by the Applicants in proof-of-principle studies using a single point probe. The data in these studies was reduced offline, and then compared with data from biopsies taken at corresponding locations. Locations were chosen randomly. After data was obtained, information about cell nuclear morphology in the LSS data needed to be extracted.

There are two principal techniques for extracting this information—subtraction of diffuse background using diffuse reflectance spectroscopy and polarization background subtraction. Diffuse reflectance spectroscopy has the advantages of retaining information about the biochemical and morphological organization of the submucosa, such as the density of the collagen matrix, and the degree of angiogenesis. Polarization background subtraction has the advantage of being less sensitive to tissue variability. The results of studies using these two techniques are discussed below.

Basic Principles of Light Scattering Spectroscopy

Applicants have developed a light scattering technique for measuring the size distribution and density of epithelial cell nuclei. As is discussed below, enlarged nuclei are primary indicators of cancer, dysplasia and cell regeneration in BE. Applicants' results, summarized below, demonstrate that the technique may accurately diagnose dysplasia clinically in the BE.

The organs of the body are lined with a thin, highly cellular surface layer of epithelial tissue, which is supported by underlying, relatively acellular connective tissue. In healthy tissues, the epithelium often includes a single, well-organized layer of cells with en-face diameter of 10-20 µm and height of 25 µm. In dysplastic epithelium, the cells proliferate and their nuclei enlarge and appear darker (hyperchromatic) when stained. LSS may be used to measure these changes. The details of the method have been published in an article by Perelman LT, Backman V, Wallace M, et al. (Observation of Periodic Fine Structure in Reflectance from Biological Tissue: A New Technique for Measuring Nuclear Size Distribution. *Phys. Rev. Lett.* 1998; 80:627-30), which is hereby incorporated in its entirety, in the Appendix.

In an example, when an incident beam of light irradiates an epithelial layer of tissue, a portion of this light is backscattered from the epithelial nuclei, while the remainder may be transmitted to deeper tissue layers, where it undergoes multiple scattering and becomes randomized before returning to the surface. Epithelial nuclei can be treated as spheroidal Mie scatters with refractive index, $n_n$ which is higher than that of the surrounding cytoplasm, $n_c$. Normal nuclei have a characteristic size of l=4-7 µm. In contrast, the size of dysplastic nuclei varies widely and can be as large as 20 µm, occupying almost the entire cell volume. In the visible range, where the wavelength of light λ<<l, the Van de Hulst approximation can be used to describe the elastic scattering cross section of the nuclei:

$$\sigma_s(\lambda, l) = \frac{1}{2}\pi l^2 \left\{ 1 - \frac{\sin(2\delta/\lambda)}{\delta/\lambda} + \left[\frac{\sin(\delta/\lambda)}{\delta/\lambda}\right]^2 \right\}, \quad (1)$$

with $\delta = \pi l(n_n - n_c)$.

Equation (1) reveals a component of the scattering cross section which varies periodically with inverse wavelength. This, in turn, gives rise to a periodic component in the tissue reflectance. Since the frequency of this variation (in inverse wavelength space) is proportional to particle size, the nuclear size distribution can be obtained from the Fourier transform of the periodic component.

To test this relationship, Applicants studied the spectra of elastic light scattering from densely packed unstained monolayers of isolated normal intestinal epithelial cells and intestinal epithelial T84 malignant cell line, affixed to glass slides in buffer solution and placed on top of a $BaSO_4$ diffusing plate, used to simulate the diffuse reflectance from underlying tissue. The spectra were then inverted to yield nuclear size distributions. The extracted and measured distributions for both normal and T84 cell samples were in very good agreement, indicating the validity of the above physical picture and the accuracy of the Applicant's method of extracting information.

Application of Light Scattering Spectroscopy to Barrett's Esophagus

Applicants observed similar periodic fine structure in diffuse reflectance from BE of human subjects undergoing gastroenterological endoscopy procedures. A schematic diagram of the proof-of-principle system 100 used to perform LSS is shown in FIG. 1. It should be appreciated that the system is shows by way of example only. System 100 comprises a fiber optic probe 102 associated with endoscope 104. A cross-sectional view 106 of fiber optic probe 102 comprising optical fibers is shown as an insert in FIG. 1. Probe 102 may be used to scan a portion, or a site, of tissue shown by way of example only as in vivo tissue 108.

In FIG. 1, a light source for fiber optic probe 102 is shown by way of example only as xenon lamp 110. Spectra of light backscattered from the portion of tissue 108 may be analyzed in a device shown by way of example only as spectrograph (spectroscope) 112. Operation of lamp 110 and spectrograph 112 may be controlled by controller 114 which is associated with a computing device 116. It should be appreciated that system 100 may comprise any other suitable components. In addition, for the convenience of the representation, not all component shown in FIG. 1 are labeled.

In this example, immediately before performing biopsy at a particular site, the reflectance spectrum from the site was collected using an optical fiber probe (e.g., fiber optic probe 102). The probe was inserted into the accessory channel of the endoscope (e.g., endoscope 104) and brought into gentle contact with the mucosal surface of the esophagus, shown in FIG. 1 as the portion of tissue 108. The probe 102 delivered a weak pulse of white light to the tissue and collected the diffusely reflected light. The probe tip sampled tissue over a circular spot approximately 1 mm$^2$ in area. The pulse duration was 50 milliseconds, and the wavelength range was 350-650 nm. The optical probe caused a slight indentation at the tissue surface that remained for 30-60 seconds. Using this indentation as a target, the site 108 was then carefully biopsied, and the sample was submitted for histologic examination. This insured that the site examined spectroscopically matched the site evaluated histologically.

The reflected light was spectrally analyzed, and the spectra were stored in a computer (e.g., computer 114 or in any other suitable computer). The spectra include a large background from submucosal tissue, on which is superimposed a small (2%-3%) component that is oscillatory in wavelength because of scattering by cell nuclei in the mucosal layer. The amplitude of this component may be related to the surface density of epithelial nuclei (number of nuclei per unit area). Because, in this example, the area of tissue probed is fixed at about 1 mm$^2$, this parameter may be a measure of nuclear crowding. The shape of the spectrum over the wavelength range may be related to nuclear size.

Figure 2:
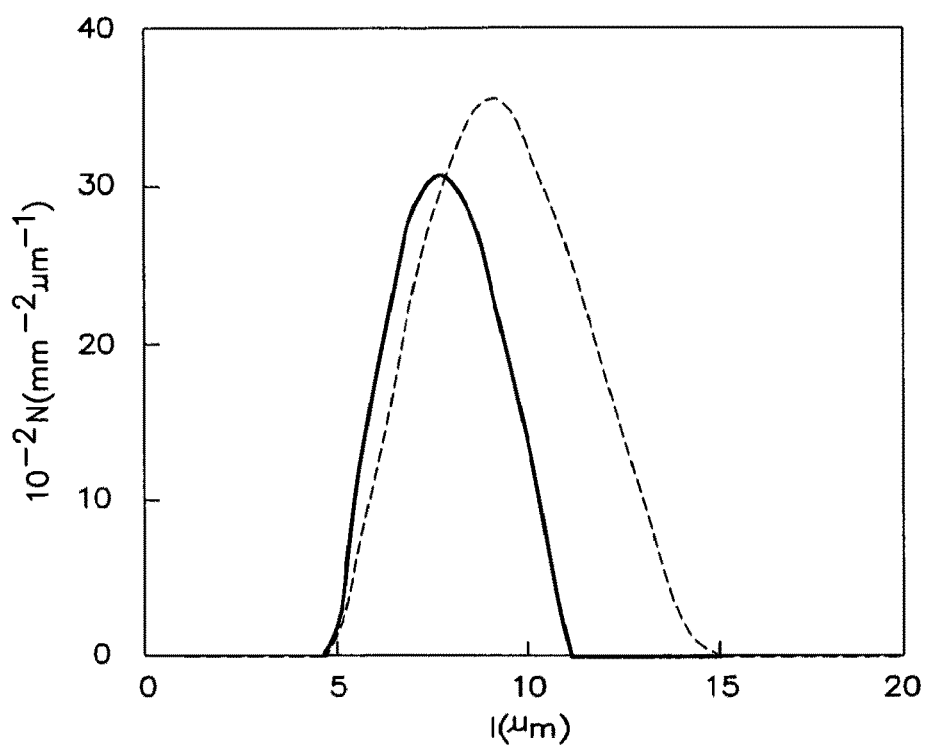
FIG. 2 is a graph of typical Barrett's Esophagus (BE) nuclear size distributions for a non-dysplastic site (solid line) and a dysplastic site (dashed line) extracted using a light scattering spectroscopy (LSS) technique.

Examples of nuclear size distributions extracted from the small oscillatory components for non-dysplastic and dysplastic BE sites appear in FIG. 2 which shows typical size distributions of nuclear volume verses nuclear diameter for a non-dysplastic site (solid line) and for a dysplastic site (dashed line). As can be seen, the difference between the distributions for non-dysplastic and dysplastic sites is pronounced. The distribution of nuclei from the dysplastic site is much broader than that from the non-dysplastic site, and the peak diameter is shifted from ~7 μm for the non-dysplastic site to about ~10 μm for the dysplastic site. In addition, both the relatively number of large cell nuclei (>10 μm) and the total number of nuclei are significantly increased. As shown by FIG. 2 LSS spectral data provides a quantitative measure of the density of nuclei close to the mucosal surface.

However, single scattering events cannot be measured directly in biological tissue. Because of multiple scattering, information about tissue scatterers is randomized as light propagates into the tissue, typically over one effective scattering length (0.5-1 mm, depending on the wavelength). Nevertheless, the light in the thin layer at the tissue surface is not completely randomized. In this thin region, the details of the elastic scattering process can be preserved. Therefore, the total signal reflected from a tissue can be divided into two parts: single backscattering from the uppermost tissue structures such as cell nuclei, and a background of diffusely scattered light. The background signal from diffusely scattered light may be removed to analyze the single scattering component of the reflected light. This can be achieved either by modeling using diffuse reflectance spectroscopy or by polarization background subtraction.

Polarization background subtraction may have the advantage of being less sensitive to tissue variability. However, the diffuse reflectance spectroscopy may have its own advantages because it can provide valuable information about biochemical and morphological organization of submucosa and degree of angiogenesis. In addition, diffuse reflectance spectroscopy can be used in combination with polarization background subtraction to extract additional potentially valuable information. Although an exemplary probe, an exemplary instrument, and an exemplary system are described herein as an LSS probe, an LSS instrument and an LSS system that uses polarization background subtraction, exemplary embodiments may be configured for LSS and/or diffuse reflectance spectroscopy, as embodiments of the invention are not limited in this respect.

Diffuse Reflectance Spectroscopy of Barrett's Esophagus

Applicants collected reflectance data for BE and developed a method for accurately modeling clinical tissue reflectance in terms of the underlying tissue scatterers and absorbers. This method provides both direct physical insight and quantitative information about the tissue constituents that give rise to the reflectance spectra. The method is summarized here. Additional details can be found in two references (Georgakoudi I, Jacobson B C, Van Dam J, et al. Fluorescence, reflectance and light scattering spectroscopies for evaluating dysplasia in patients with Barrett's esophagus. *Gastroentorolgy* 2001; 120:1620-9 and Zonios G, Perelman L T, Backman V, et al. Diffuse Reflectance Spectroscopy of Human Adenomatous Colon Polyps In Vivo. *Applied Optics* 1999; 38:6628-37), each of which is incorporated herein in its entirety, in the Appendix.

Applicants created an analytical model, using the diffusion approximation, to describe the tissue reflectance spectrum collected by a finite sized probe with an effective radius $r_c$. Biological tissue is treated as a homogeneous medium with wavelength-dependent absorption coefficient $\mu_a$ and reduced scattering coefficient $\mu'_s$. Incident photons are scattered and absorbed in the tissue, with the surviving scattered photons eventually escaping from the tissue surface. A fraction of the escaping diffusely reflected light is collected by the probe.

A simple analytical expression for the diffuse reflectance collected by the probe is $$R = \frac{1}{2}a'\left[e^{-x} + e^{-\eta x} - \frac{e^{-r_1 x}}{r_1} - \frac{e^{-\eta r_2 x}}{r_2}\right], \quad (2)$$

with $a' = s/(a+s)$, $x = \sqrt{3(1-a')}$, $r_1 = \sqrt{1+(a+s)^2}$, $r_2 = \sqrt{1+[(a+s)/\eta]^2}$, $\eta \approx 5.3$, $a = \mu_a r_c$, $s = \mu'_s r_c$.

For a given probe geometry there is an -optimal value of $r_c$, the effective probe radius, which can be determined by calibrating Eq. (2) using the reflectance measurement of a tissue phantom with known optical properties. For the visible tissue reflectance spectra collected in BE, hemoglobin (Hb) was found to be the only significant light absorber. To account for both oxygenated and deoxygenated forms of Hb, the total absorption coefficient, $\mu_a(\lambda)$ is given by $$\mu_a(\lambda) = \ln 10 c_{Hb} [a \epsilon_{HbO_2}(\lambda) + (1-a) \epsilon_{Hb}(\lambda)] \quad (3)$$

where a is the Hb oxygen saturation parameter and $C_{Hb}$, the total hemoglobin concentration. The wavelength dependent extinction coefficients (i.e., the $\epsilon$'s) of both forms of hemoglobin are known.

To test the above model, the reflectance spectra of a series of tissue phantoms with known absorption and scattering properties were measured. Aqueous suspensions of polystyrene spheres were used to simulate scatterers, and hemoglobin was used for absorption. Concentrations and bead size were chosen to provide absorption and scattering properties that covered the range for human BE tissue. Mie theory was used to obtain the reduced elastic scattering cross-section, as $\sigma'_s(\lambda)$, of the spheres.

The phantom reflectance spectra were accurately modeled by Eq. (2), using the known absorption and scattering coefficients. By fitting Eq. (2) to experimental phantom data obtained using various values of Hb concentration, oxygen saturation, scatterer size, and scatterer density, the values of these parameters were recovered with accuracy of better than 10% over the full range of the four parameters. This established that the experimental spectra are adequately described by Eq. (2), and that this expression could be used in an inverse manner to extract the parameters from the spectra with reasonable accuracy.

Diffuse reflectance spectra were collected from BE sites as described below. The clinical data were analyzed using Eq. (2) and the known spectra of oxy- and deoxy-hemoglobin to extract values of Hb concentration and saturation, and $\mu'_s$. For biological tissue, the reduced scattering coefficient ($\mu'_s$) is the sum of contributions from the various tissue scatterers. Detailed information about these individual scatterers may not be available. Therefore, the reduced scattering coefficient may be defined as follows:

$$\mu'_s(\lambda) = \rho_s \sigma'_s(\lambda), \quad (4)$$

with $\rho_s$, the effective scattering density and $\sigma'_s(\lambda)$ the effective reduced scattering cross section. With this, tissue scattering properties are modeled in an average way, as if tissue contained a single well-defined type of scatterer. In general, $\sigma'_s(\lambda)$ depends on the refractive index, shape and size of the scatterer, as well as on the refractive index of the surrounding medium. Mie scattering theory is used to evaluate $\sigma'_s(\lambda)$, assuming the scatterers to be homogeneous spheres of diameter $d_s$ and relative refractive index n, $\sigma'_s(\lambda)$.

Figure 3:
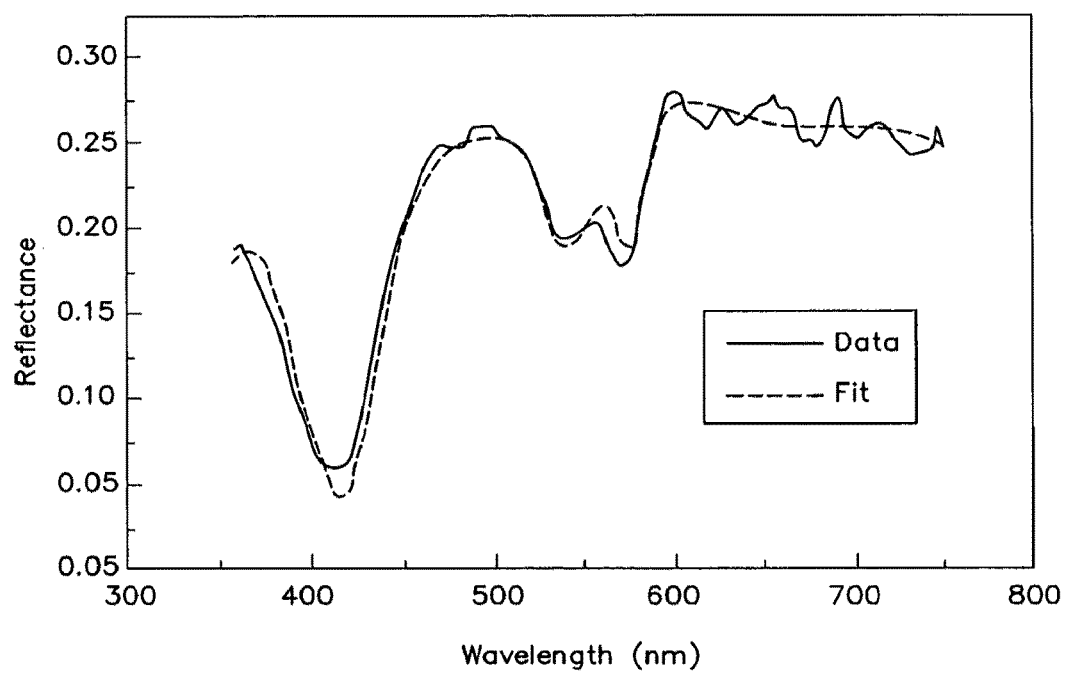
FIG. 3 is a graph of a reflectance spectrum of a nondysplastic BE site showing experimental data (solid line) and a model fit to the experimental data (dashed line)

FIG. 3 shows typical diffuse reflectance spectra from one nondysplastic BE site. As shown, model fits are excellent. Both the absorption dips and scattering slopes are sensitive functions of the fit parameters, providing an inverse algorithm that is sensitive to such features. An inverse algorithm was applied to the clinical spectra, obtaining values of the four parameters for each site probed. These parameters provide valuable information about the tissue properties.

Figure 4A:
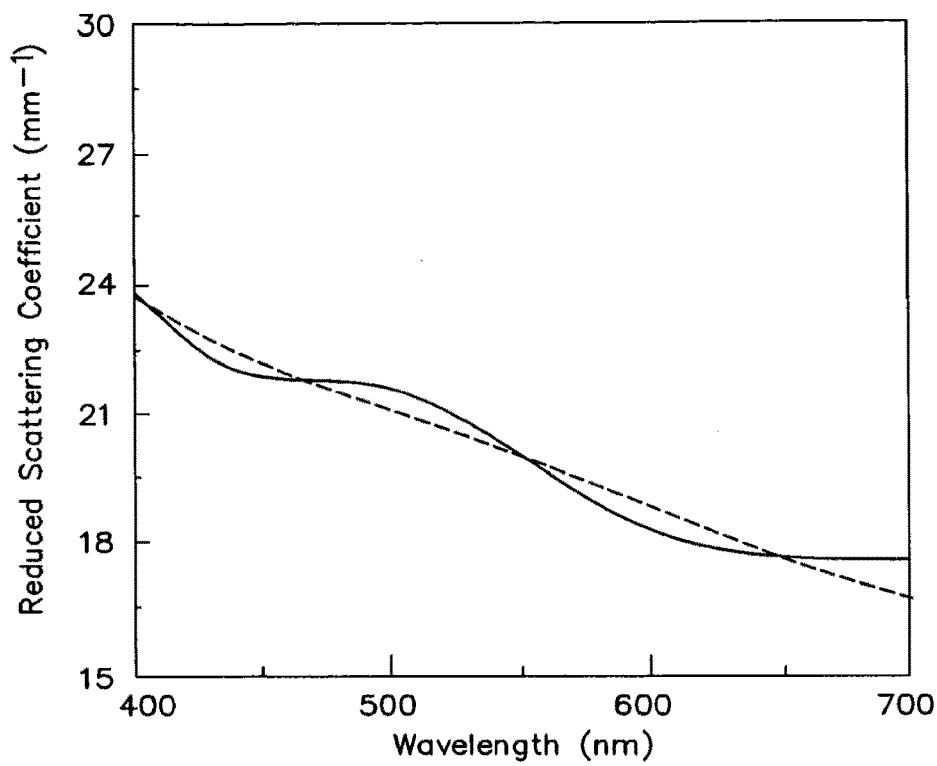
FIG. 4A is a graph of a reduced scattering coefficient as a function of wavelength for a representative nondysplastic BE site (solid line) and a corresponding linear fit (dashed line)
Figure 4B:
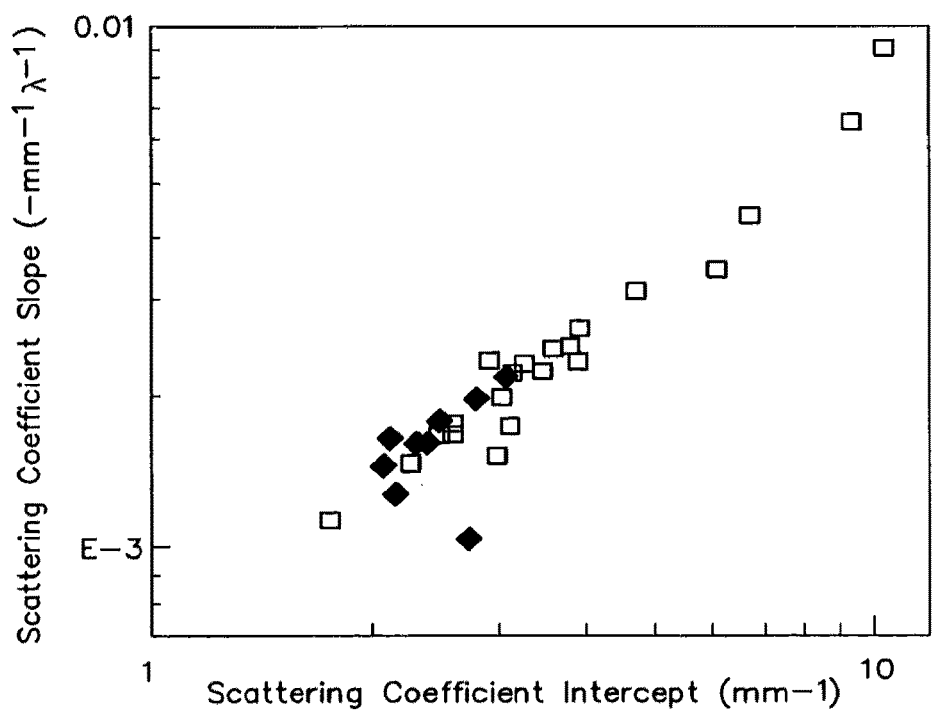
FIG. 4B is a graph of slope and intercept obtained from a linear fit to wavelength-dependent tissue reduced scattering coefficients, $\mu_s'$, for nondysplastic (squares), low-grade dysplastic (solid diamonds), and high-grade dysplastic (circles) BE sites displayed on a log-log scale.

This analysis establishes that the reduced scattering coefficient, $\mu_s'$, of Barrett's esophagus tissue changes gradually during the progression from nondysplastic, to low-grade dysplasia, to high-grade dysplasia, as shown in FIG. 4A. For example, at 400 nm, the $\mu_s'$ of high-grade dysplastic (HGD) tissue (1.3±0.2 mm$^{-1}$) is lower than that of low-grade dysplastic (LGD) tissue (1.8±0.3 mm$^{-1}$), which, in turn, is lower than that of nondysplastic BE (NDB) tissue (3±1.6 mm$^{-1}$). Additionally, the wavelength dependence of $\mu_s'$ changes during the development of dysplasia. To describe these changes, a straight line is fit to $\mu_s'(\lambda)$. The intercept of the line at 0 nm and the slope of the line can be used as additional two LSS diagnostic parameters as shown in FIG. 4B.

Applicants' analysis indicates that the scattering coefficient of tissue decreases significantly during the development of dysplasia, suggesting that changes that are not observed histopathologically are taking place within the lamina propria and submucosa before the onset of invasion. Recently, it has been shown that an increased level of cysteine and serine proteases is found in gastric and colorectal cancerous and precancerous lesions. Applicants' findings related to the decrease in the value of the scattering coefficient during the progression of dysplasia are consistent with the presence of such enzymes, which could result in a less dense collagen matrix, for instance. The change in the slope of $\mu_s'$ as a function of wavelength suggests that the mean size of the tissue scattering particles is changing. Crowding of the cells and nuclei of the epithelial layer may be responsible for this change.

Thus, Applicants observed that diffuse reflectance spectroscopy can be used to obtain quantitative information about structural composition of connective tissue in vivo. Diffuse reflectance spectroscopy may provide additional quantitative information about tissue scatterers and absorbers.

Polarization Background Subtraction

When tissue is illuminated with a polarized light, the light backscattered from the superficial epithelial layer of the tissue retains its polarization, i.e. it is polarized parallel to the incoming light. The light backscattered from the deeper tissues becomes depolarized and contains about equal amounts of parallel and perpendicular polarizations. By subtracting the signal with parallel polarization from the signal with perpendicular polarization (or vice versa), the signal contribution from scattering off of deeper tissues can removed and the resulting signal is proportional only to the signal from the superficial epithelial layer, which contains the information about early precancerous changes.

Figure 5A:
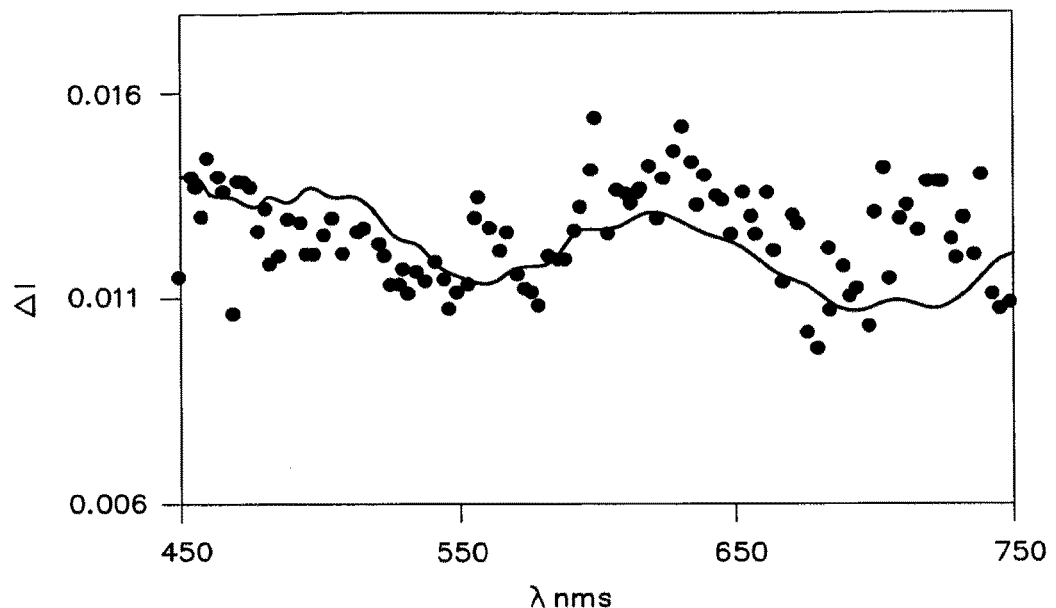
FIG. 5A is a graph of a spectrum of a polarized component of back scattered light from normal intestinal cells.
Figure 5B:
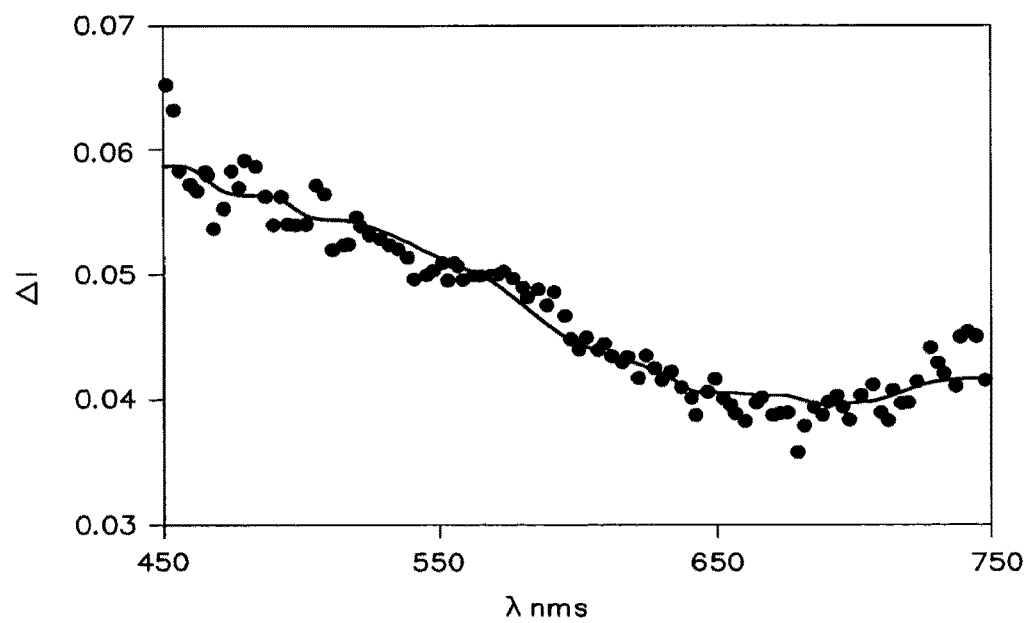
FIG. 5B is a graph of a spectrum of a polarized component of back scattered light from T84 intestinal malignant cells.
Figure 5C:
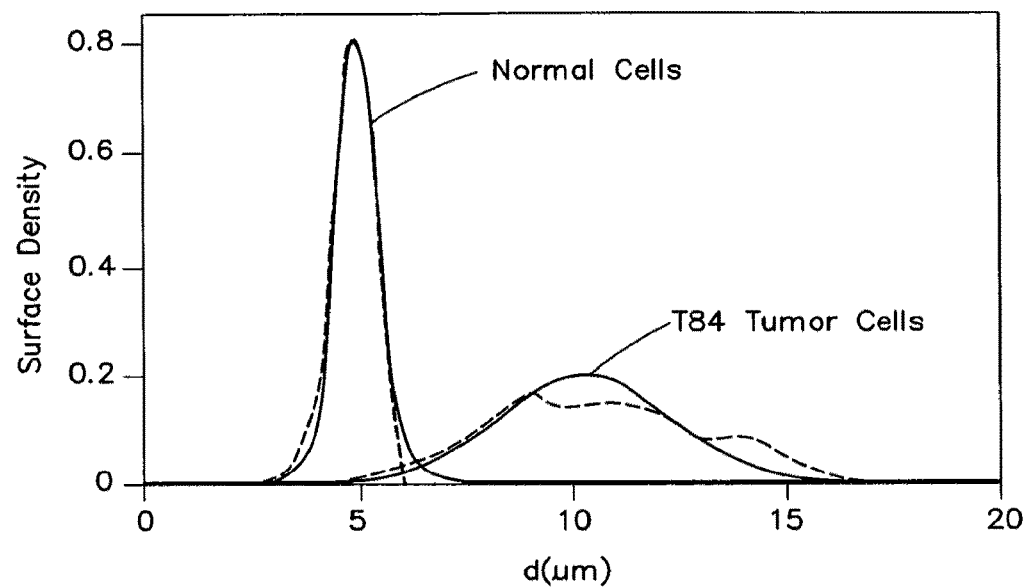
FIG. 5C is a graph of nuclear size distributions obtained from the spectra shown in FIGS. 5A and 5B, where the distributions extracted from the LSS data are shown with solid lines and the distributions measured using light microscopy are shown with dashed lines.

FIGS. 5A through 5C demonstrate that polarization background subtraction can efficiently cancel the diffuse component of the scattering signal and the residual signal can be analyzed using standard LSS procedure. FIG. 5A shows a spectrum of intensity of a polarized component of backscattered light as a function of wavelength for normal intestinal cells, and FIG. 5B shows a spectrum for T84 intestinal malignant cells. FIG. 5C shows distributions of cell nuclei extracted from the spectra where the solid line is the distribution extracted from the spectral data and the dashed line is the distribution measured using light microscopy. As illustrated by FIG. 5C, spectra of polarized components of backscattered light provide information about nuclear size distributions, which can be used to differentiate normal cells from malignant cells.

Clinical Detection of Dysplasia in Barrettes Esophagus Using Light Scattering Spectroscopy The first clinical application of this method was conducted at the Brigham and Women's Hospital and the West Roxbury Veterans Administration Medical Center. The protocol was approved by the Institutional Review Boards of both hospitals. Data were collected from 16 patients with known BE undergoing standard surveillance protocols. After informed consent, consecutive patients undergoing surveillance endoscopy for a diagnosis of Barrett's esophagus or suspected carcinoma of the esophagus were evaluated by systematic biopsy. In surveillance patients, biopsy specimens were taken in 4 quadrants, every 2 cm of endoscopically visible Barrett's mucosa. In patients with suspected adenocarcinoma, biopsy specimens for this study were taken from the Barrett's mucosa adjacent to the tumor. Measurements were performed using a proof-of-principle LSS system shown in FIG. 1. The results are summarized below.

TABLE 1

|  | κ | % Agreement |
|---|---|---|
| Pathologist 1 vs. colleagues | 0.31 | 66 |
| Pathologist 2 vs. colleagues | 0.22 | 62 |
| Pathologist 3 vs. colleagues | 0.34 | 65 |
| Pathologist 4 vs. colleagues | 0.37 | 65 |
| Spectroscopy vs. pathology, average diagnoses | 0.57 | 80 |
| Spectroscopy vs. pathology, consensus diagnoses | 0.63 | 90 |

Additional details can be found in an article by Wallace M., Perelman L. T., Backman V., et al. (Endoscopic Detection of Dysplasia in Patients With Barrett's Esophagus Using Light Scattering Spectroscopy: A Prospective Study. *Gastroentorolgy* 2000; 119:677-82), which is incorporated herein in its entirety, in the Appendix.

Table 1 shows interobserver agreement between individual pathologists and the average diagnoses of the 3 other pathologists and agreement between the multivariate LSS model and the average diagnosis of all 4 pathologists. To establish diagnostic criteria, 8 samples were selected as a "modeling set", and the extracted nuclear size distributions were compared to the corresponding histology findings. From this, sites were classified as dysplasia if more than 30% of the nuclei were enlarged, with "enlarged" defined as exceeding a 10 µm threshold diameter, and classified as non-dysplasia otherwise. The remaining 68 samples were analyzed using this criterion. Averaging the diagnoses of the four pathologists, the sensitivity and specificity of detecting dysplasia were both 90%, with dysplasia defined as low grade dysplasia (LGD) or high-grade dysplasia (HGD), and non-dysplasia defined as (non-dysplasia Barrett's) NDB or indefinite for dysplasia (IND). The sensitivity and specificity were excellent, given the limitations of interobserver agreement among pathologists.

Figure 6:
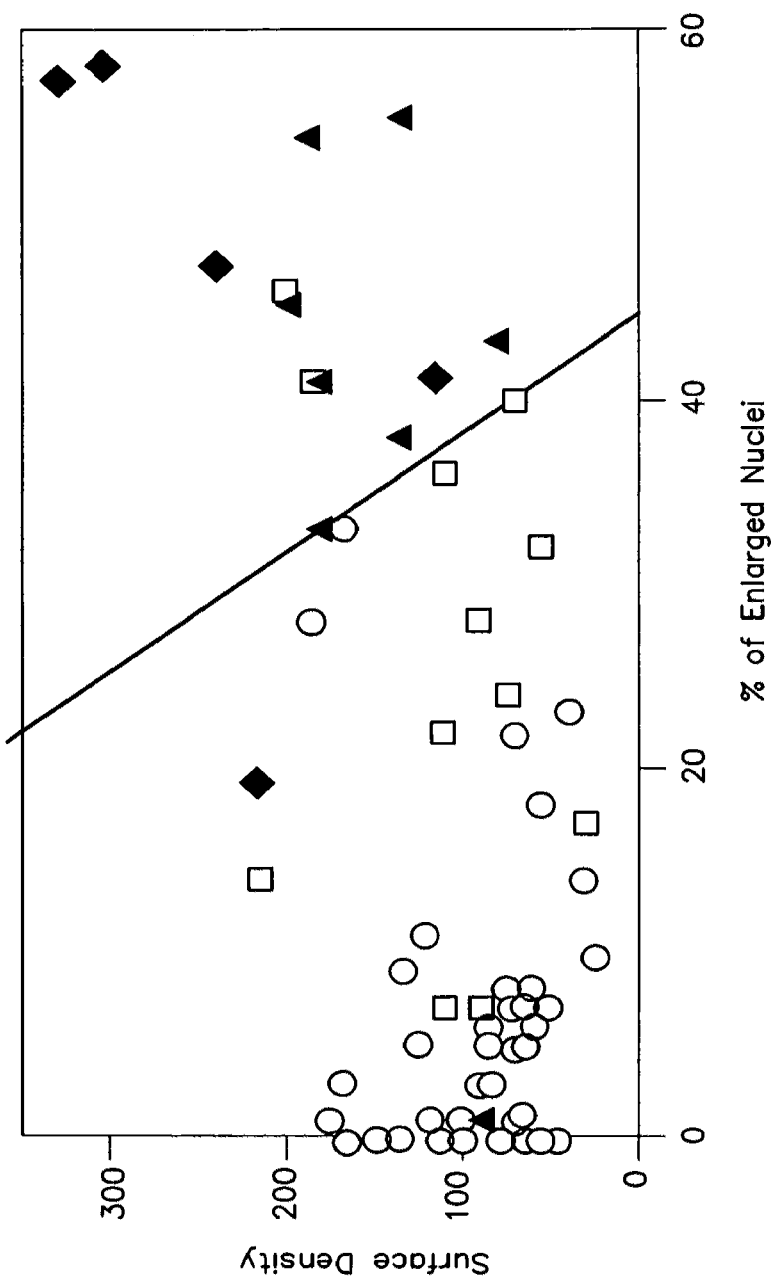
FIG. 6 illustrates an LSS diagnostic plot of Barrett's esophagus (BE) data including: nondysplastic BE (NDB-circles); indefinite for dysplasia (IND-squares); low-grade dysplasia (LGD-triangles) high-grade dysplasia (HGD-diamonds); and an exemplary decision threshold for dysplasia (line), in accordance with some aspects of the invention.

To further study the diagnostic potential of LSS, the entire data set was then evaluated adding a second criterion, the population density of surface nuclei (number per unit area), as a measure of crowding. The resulting binary plot is shown in FIG. 6, in which NDB is shown with circles, IND is shown with squares, LGD is shown with solid triangles, and HGD is shown with solid diamonds. The plot reveals a progressively increasing population of enlarged and crowded nuclei with increasing histological grade of dysplasia, with the NDB samples grouped near the lower left corner and the HGD samples at the upper right. Using logistic regression, the samples were then classified by histologic grade as a function of the two diagnostic criteria.

The percentage agreements between LSS and the average and consensus diagnoses (at least 3 pathologists in agreement) were 80% and 90%, respectively. This is much higher than that between the individual pathologists and the average diagnoses of their 3 colleagues, which ranged from 62 to 66%, and this was also reflected in the kappa statistic values appearing in Table 1.

Applicants' results demonstrate that LSS can be used in a minimally invasive instrument for accurately and reliably classifying invisible dysplasia in BE in vivo.

Endoscopic Polarized Spectroscopic Scanning Instrument

While methods of illuminating a single point of tissue of an organ may allow detecting changes in the tissue, scanning and/or wide field modalities may be required for guiding biopsy in realistic clinical settings. EPSS is distinguished among other techniques of detecting precancerous changes in various organs (e.g., esophagus, colon, pancreas, biliary duet, cervix, stomach, small intestine, large intestine, rectum and others) by its ability to locate dysplasia in tissue which otherwise shows no visible abnormalities or lesions. By elucidating microscopic subcellular structure with macroscopic spectral measurements, EPSS may locate dysplastic tissue independent of any visual cues.

As discussed above, LSS-based detection of dysplasia in BE has been demonstrated successfully by the Applicants using a simple proof-of-principle instrument that was capable of collecting single-point data at randomly selected sites, which then were biopsied. The data was processed offline, and a comparison with the biopsy results was made at a later time. The high correlation between spectroscopic results and pathology was sufficiently promising to justify development of a clinical LSS endoscopic scanning instrument.

Figure 7:
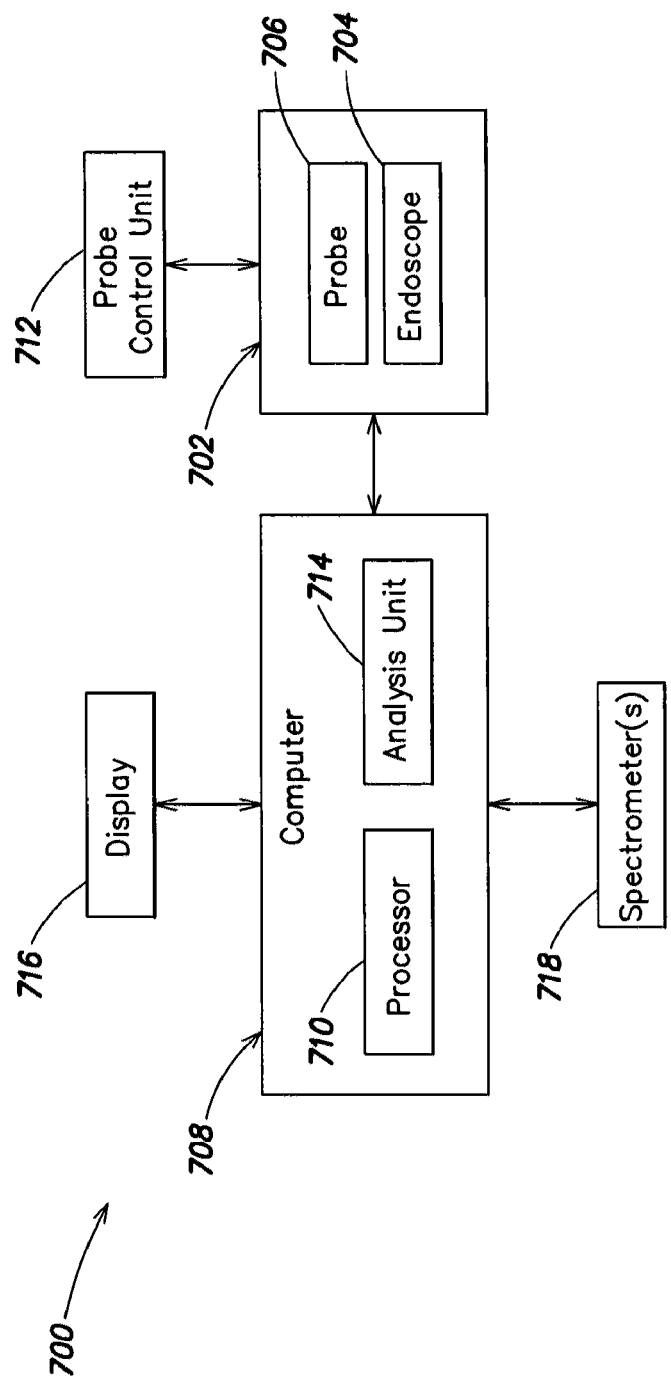
FIG. 7 illustrates a polarized LSS endoscopic polarized scanning spectroscopic instrument (EPSS) in accordance with an embodiment of the invention.

Reference is now made to FIG. 7, which illustrates an exemplary EPSS system 700 in accordance with aspects of the invention. The EPSS system 700 includes a polarized LSS endoscopic scanning instrument 702 that may comprise an endoscope 704, a probe 706 (e.g., fiber optic probe 102 shown in FIG. 1) and any other suitable components. Endoscope 704 may comprise any suitable components. Thus, endoscope 704 may comprise one or more components (e.g., an imaging unit) for imaging (e.g., video imaging) surface that is being scanned. Similarly, probe 706 may comprise any suitable components. It should be appreciated that embodiments of the invention are not limited to any particular endoscope or a probe.

In some embodiments, the EPSS system 700 may be compatible with existing endoscopes and may scan any esophageal area chosen by the physician and executes software necessary to obtain quantitative, objective data about tissue structure and composition, which can be translated into diagnostic information in real time, thus providing the location of otherwise invisible HGD in vivo and serving as a guide for biopsy. In other embodiments, the EPSS system 700 may incorporate its own dedicated endoscope. The EPSS 700 may be used to scan large areas of the esophagus. The system enables the physician to take confirming biopsies at suspicious sites, reduces the number of biopsies taken at non-dysplastic sites, reduces the time and labor involved in screening and diagnosis, causes less subject discomfort and ensures reliable detection of pre-cancerous lesions.

In some embodiments, the EPSS system 700 may include a computing device 708. (e.g. a computer) comprising one or more processors 710 and other suitable components. Computing device 708 may be configured to execute, by one or more processors 710, code to generate analysis data comprising image and diagnostic information. The information may comprise quantitative, objective information about tissue structure and composition from obtained spectroscopic data. By way of example only, computer 708 is shown to comprise analysis unit 714 which may be used to execute the code to generate the analysis data. The code may be stored in analysis unit 714, in other component of computing device 708, or in any other suitable location. In some embodiments, the analysis data may be stored externally to computer 708. In addition, analysis unit 714 may be associated with one or more spectrometers, with processor 710 or with any other suitable component.

The system 700 may also comprise probe control unit 712 used to control operation of probe 706. The system 700 may also include at least one display device 716 for displaying image and diagnostic information. Display device 716 may comprise any suitable user interface to present the image and diagnostic information and any other suitable information to a user.

In this example, the code executing on the computing device 708 (e.g., the code in analysis unit 714), may permit spectroscopy data to be translated into diagnostic information in real time during an endoscopy procedure. The diagnostic information may be displayed to a physician on the display device 716 during the procedure enabling the physician to take confirming biopsies at suspicious sites and reduce the number of biopsies taken at non-dysplastic sites.

In some embodiments of the invention, the outer surface of probe 706 (e.g., the EPSS probe) may be made of any suitable material. For example, the probe may be made of stainless steel, parylene-coated torque tube which provides rotary and linear scanning via probe control unit 712 with stepper motors. In one embodiment, two stepper motors (e.g., a liner drive motor and a rotary drive motor) may be employed. The probe 706 may comprise of a delivery fiber and receiver fiber polarized in parallel and a second receiver fiber polarized orthogonally. The probe 706 may also comprise a parabolic mirror at the probe distal tip that may collimate the illumination beam and ensure maximum overlap of the three visual fields at around 11 mm from the probe axis, the radius of a typical adult human esophagus. Light may be emitted approximately 70 degrees proximal to the probe axis to avoid specular reflections. The system 700 may also include one or more spectrometers 718 for analyzing spectra of light backscattered from tissue illumined during scanning.

Although an embodiment of the EPSS system 700 is discussed primarily with respect to using the polarization technique to extract diagnostic information about dysplasia, embodiments of the system may also be used to sum the two polarizations to permit the application of diffuse reflectance spectroscopy, which can provide information about early stages of adenocarcinoma.

In some embodiments, a EPSS system may allow a user to scan the esophagus or any other organ of a patient to obtain quantitative, objective data about tissue structure and composition over a two-dimensional area. The contained data about the tissue may be translated into diagnostic information. The diagnostic information may be used to guide biopsy in real time.

In some embodiments, a EPSS instrument employs collimated illumination and collection optics that enable the instrument to collect data for generating maps of epithelial tissue that may not be affected by the distance between a probe tip of the instrument and the mucosal surface. This may make the instrument less sensitive to peristaltic motion.

In some embodiments, a EPSS system may incorporate a polarizer for removing unwanted background in the LSS signal and single backscattering in the diffuse reflectance spectroscopy signal. In some embodiments, the EPSS system may be used in both an LSS signal mode and in a diffused reflectance spectroscopy mode. In some embodiments, a EPSS system may combine both LSS information and diffuse reflectance spectroscopy information to provide a diagnostic assessment to a clinician.

Figure 8:
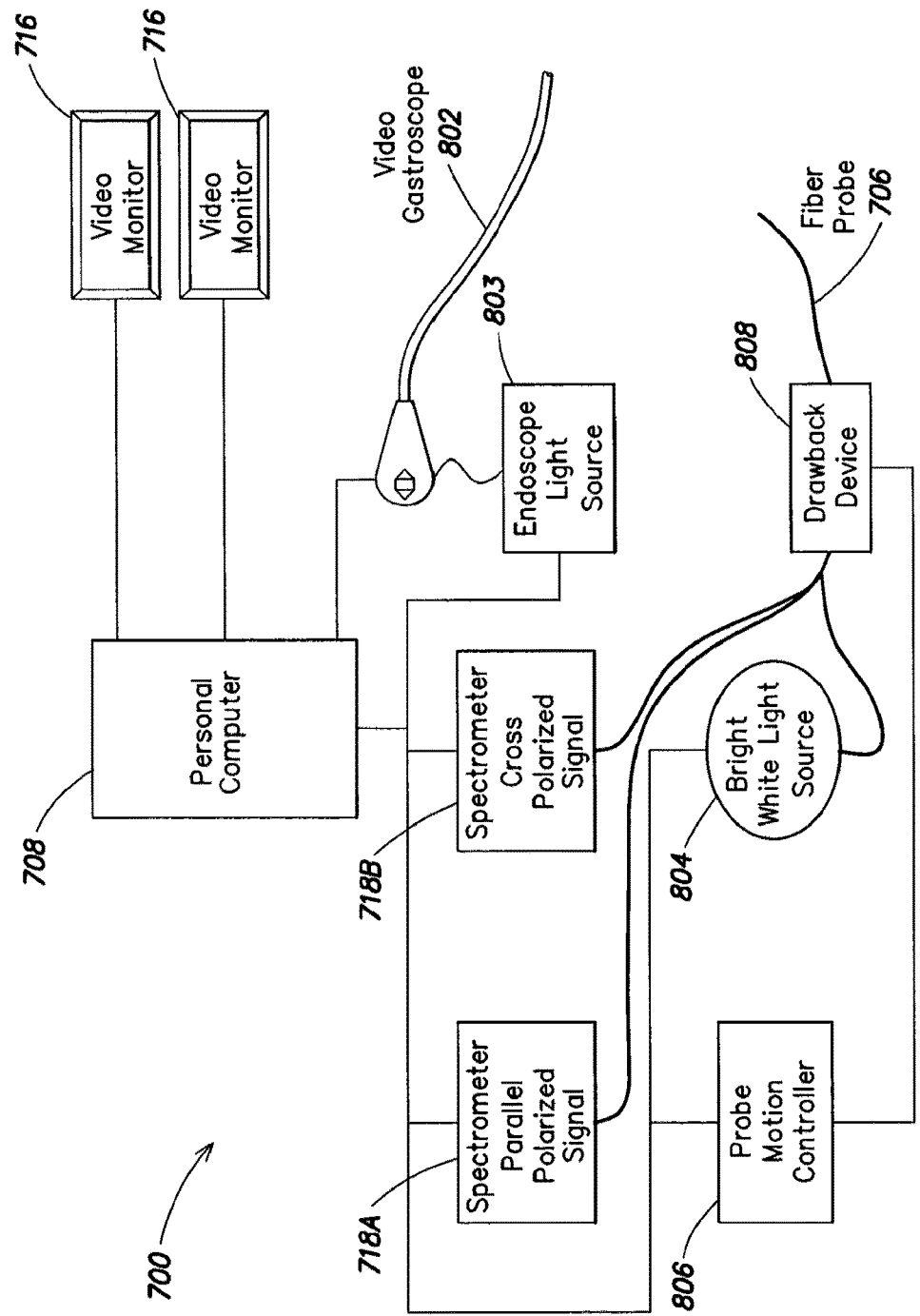
FIG. 8 is a schematic block diagram of an EPSS system in accordance with some aspects of the invention.
Figure 9:
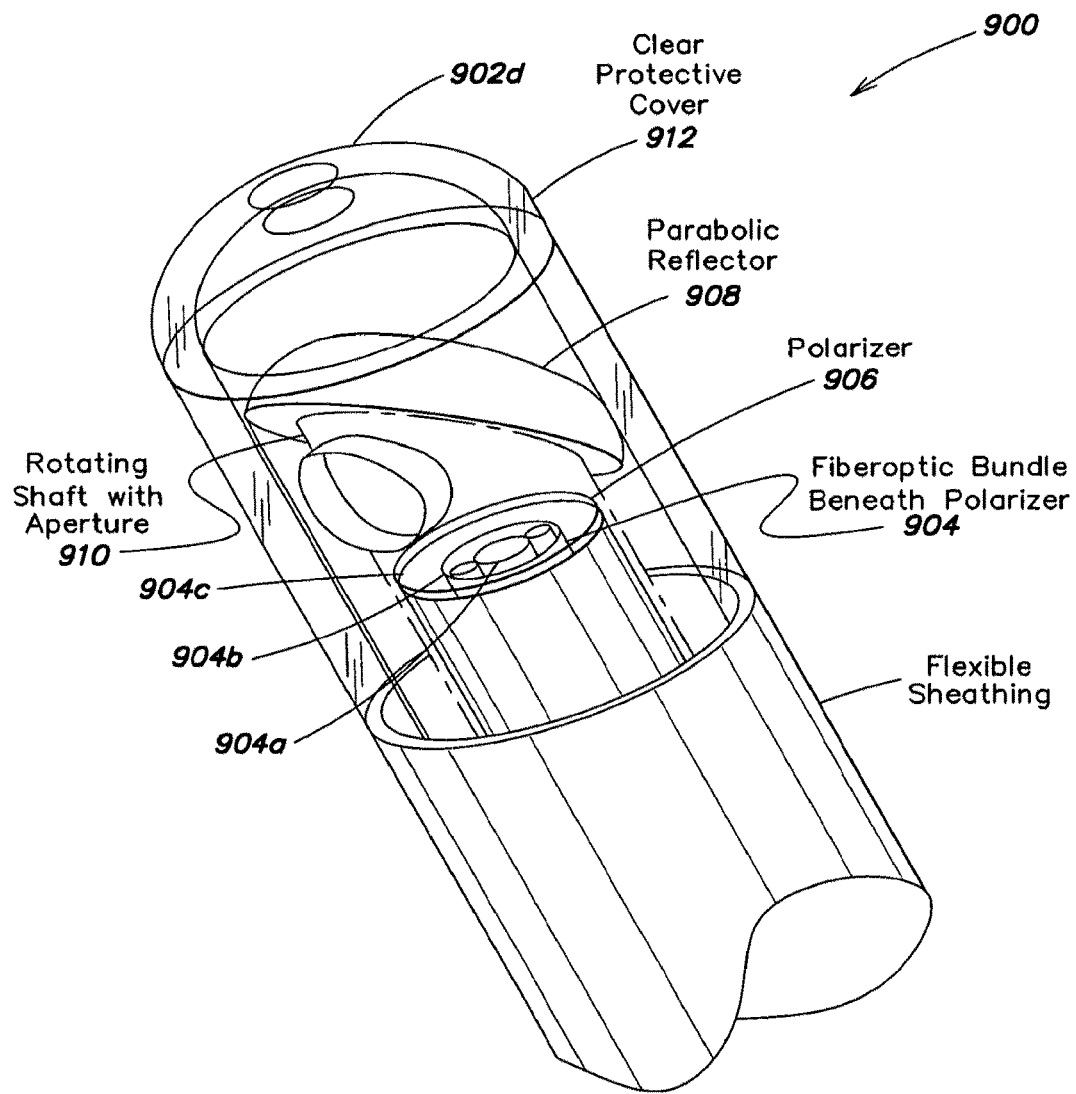
FIG. 9 is a schematic perspective view of a portion of a scanning polarization probe in accordance with aspects of the invention.

As shown in the schematic block schematic of FIG. 8, an exemplary EPSS system 700 may comprise fiberoptic probe 706. During a procedure the fiberoptic probe 706 is inserted into an instrument channel of a device 702 such as a gastroscope 802. Gastroscope 802 is shown as a video gastroscope to indicate that gastroscope 802 is configured to collect image data (e.g., video images) on scanned portions of tissue. The device may be associated with a light source shown by way of example only as endoscope light source 803. Light source 803 may be coupled in any suitable manner (e.g., optically) with gastroscope 802. The system 700 may also include spectrometers 718 such as a spectrometer 718A for a parallel polarized signal, and a spectrometer 718B for a cross polarized signal. The system 700 may also comprise a light source 804, shown by way of example only as bright white light source, for supplying light to the probe. It should be appreciated that, although light source 804 is labeled as a bright white light source, exemplary systems may include additional or other types of light sources of different wavelength bands, as embodiments the invention are not limited in this respect.

The system 700 may also include a probe motion controller 806 (e.g., probe control unit 712) for controlling a scanning motion of a portion of the probe with respect to the gastroscope 802. The probe motion controller 806 may control operation of the probe automatically. However, the probe may be controlled manually, or in any combination of manual and automatic controlling. The system 700 may also include a device referred to as drawback device 808 for translating the probe with respect to a gastroscope. The system 700 may use, for example, commercially available gastroscopes and video processors. A standard personal computer 708 may be adapted to control the system. Commercially available spectrometers may also be adapted for use with the system.

As described above, a probe of the EPSS system may be configured to scan with respect to a gastroscope 802. Further details regarding an exemplary scanning polarization probe 900 (e.g., probe 706) are described with respect to FIG. 9. At its proximal end, the scanning polarization probe 900 may be coupled to light source 720 and spectrometer 718A. During a clinical procedure a distal end portion 902d of the probe 900 may be passed through a 2.8 mm diameter working channel of a standard gastroscope 704 to access the esophagus. All exposed probe materials may be biocompatible and sterilizable by an acceptable method. In one exemplary embodiment, the length of the probe may be 3 meters with a trifurcation section of approximately 1 meter. The probe 900 may comprise 3 optical fibers 74 with SMA proximal connectors 905 (shown in FIG. 11) to attach one large 400 μm core diameter delivery optical fiber 904a to a broadband light source and two collection fibers 904b, 904c to the spectrometer channels. See also FIG. 11. The delivery fiber 904a carries light to the distal end portion 902d tip of the probe. At the probe's distal end portion 902d, light exiting the fiber passes through a linear polarizer 906 and then a rotating mirror 908, which may be a parabolic mirror (parabolic reflector), projects the light about the circumference of the esophagus. In one exemplary embodiment, the probe may project a 1-3 mm (depending on the distance of the probe from the esophageal wall) spot of linearly polarized white light (wavelengths from 400 to 800 nm), at an angle of incidence of ~17° to 20°, onto the esophageal wall from the center of the esophagus.

The probe 900 may be configured to enable rotating (scanning) the beam (i.e. moving the nominal 2 mm spot) continuously about the circumference of the esophagus and/or retracting with the same 2 mm steps to cover a BE section of interest. The mirror 908 may be coupled to a rotating shaft 80. The rotating shaft 910 may have an aperture through which the incident light beam passes. The probe 900 may also include a protective cover 912 for protecting an end portion of the rotating shaft 910.

Figure 10:
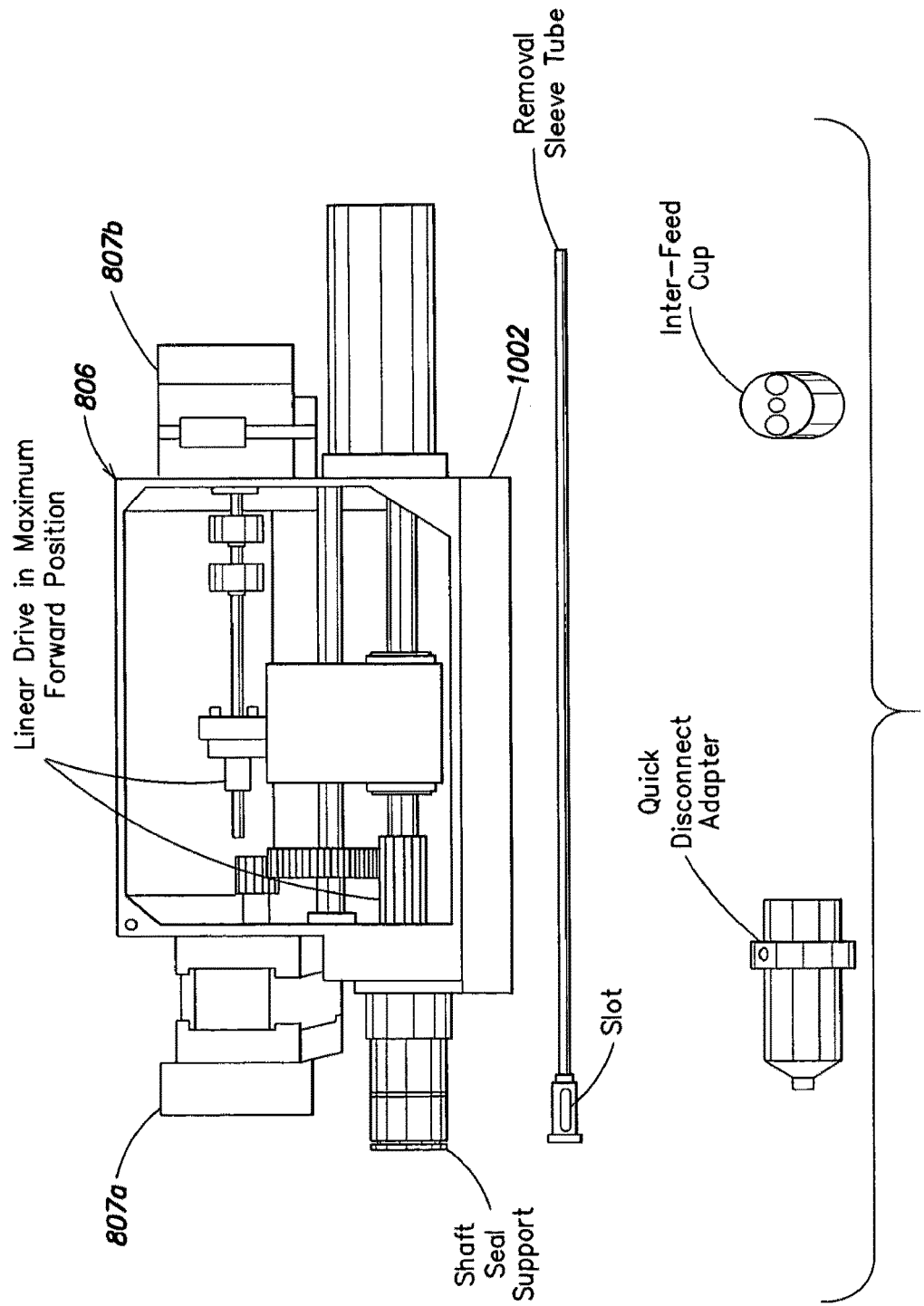
FIG. 10 illustrates components of a control unit for a probe in accordance with some aspects of the invention.
Figure 11:
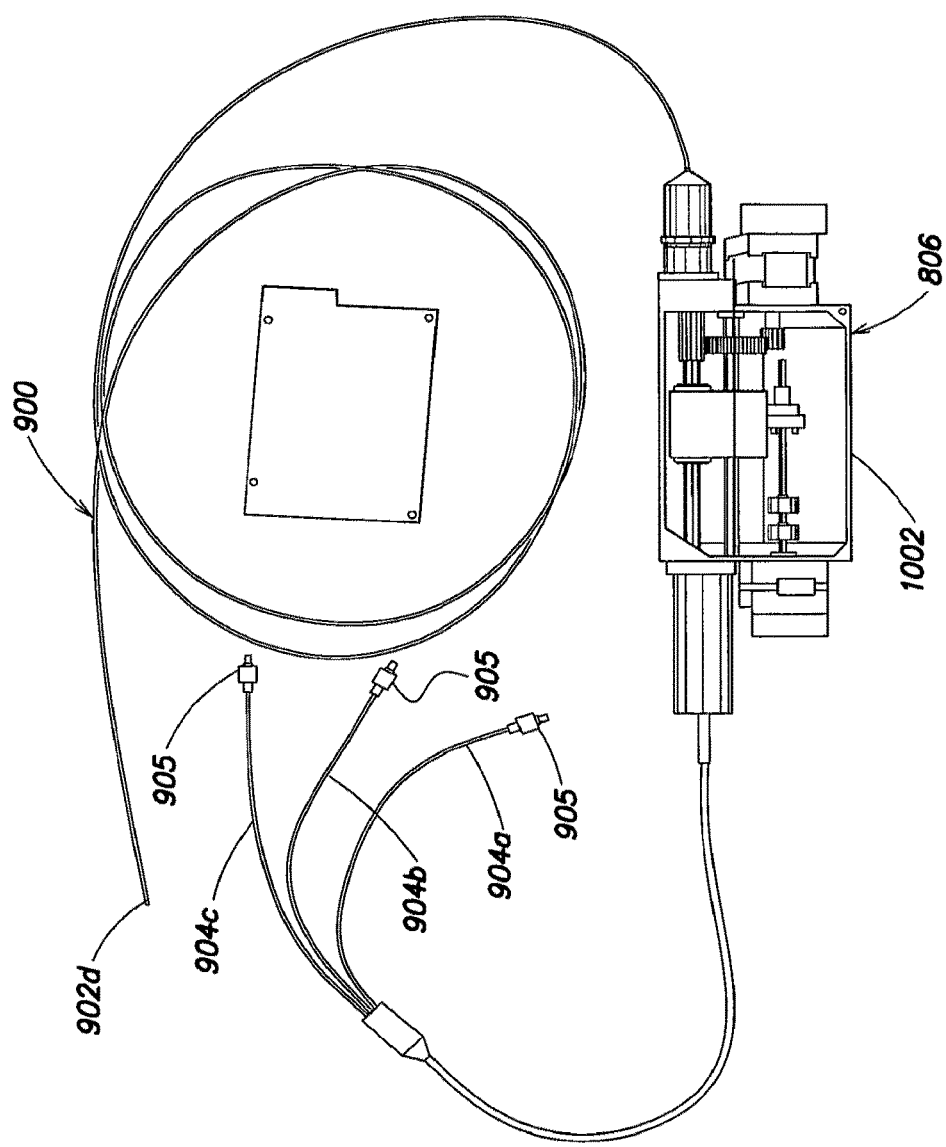
FIG. 11 illustrates a scanning polarization probe and control unit in accordance with aspects of the invention.

In some embodiments of the invention, the probe 900 may be rotated and retracted using, for example, a probe motion controller unit 806. In one embodiment, the controller unit 806 may include two stepper motors 807a, 807b located inside a control box 1002, as shown in FIG. 10. The controller unit 806 may itself be controlled by a computer, for example using a software interface such as LABVIEW or any other suitable software, hardware or combination thereof. The commands of the controller unit 806 may be synchronized with the scanning of the illumination fibers and the data captured by the spectrometers. The assembled scanning polarization probe 900 and control box 1002 are shown in FIG. 11.

User Interface

Figure 12:
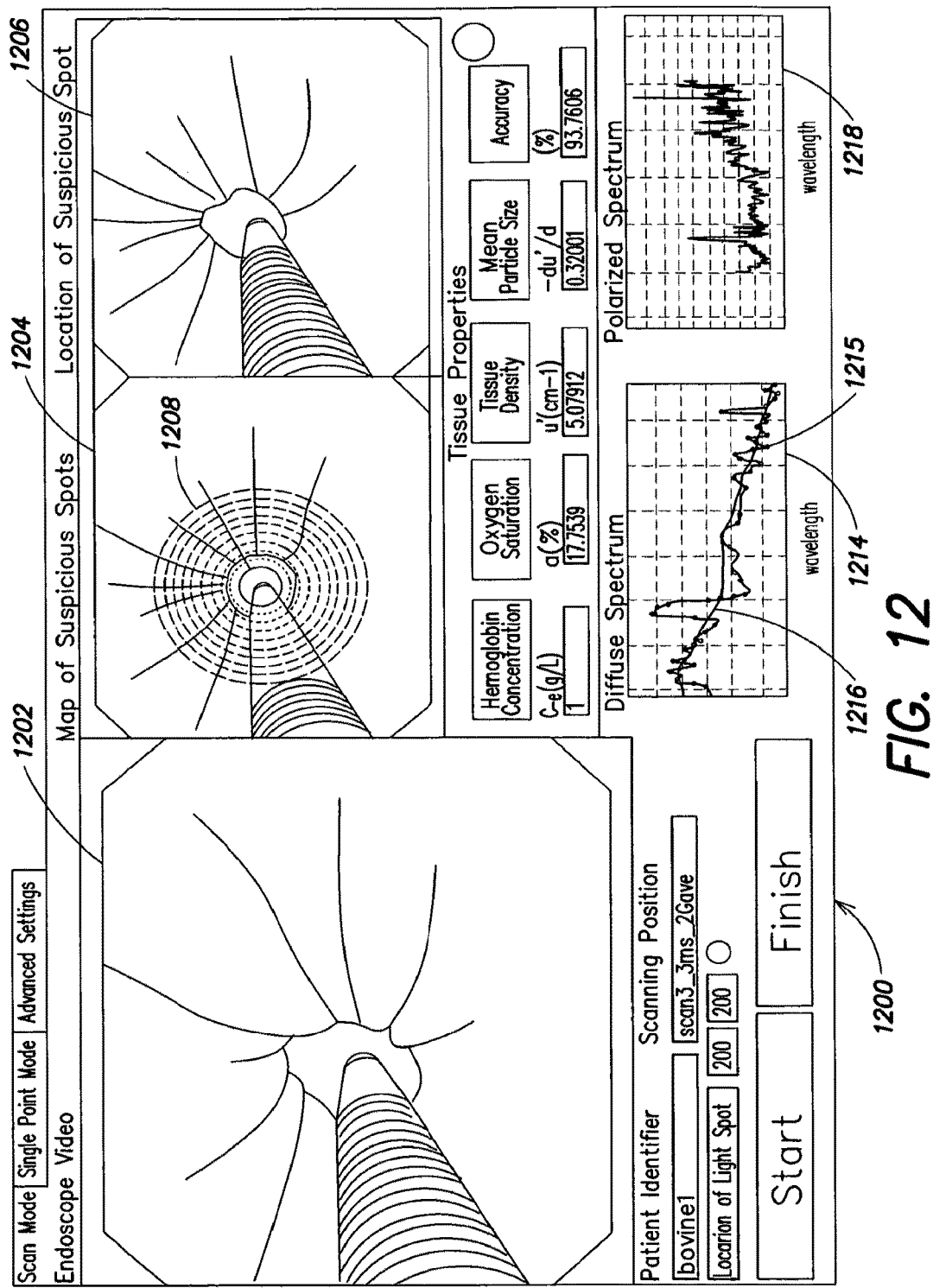
FIG. 12 illustrates a user interface for an endoscopic polarized scanning spectroscopic (EPSS) instrument, in accordance with other aspects of the invention.

As described above, a EPSS system may include a computing device and a display for interacting with a user. The system may be programmed to execute code for providing a user interface 1200 of the polarized LSS endoscopic scanning instrument, as shown in FIG. 12. The user interface 1200 may include pseudocolor maps that provide information about cellular and subcellular structure. Such information may include, but is not limited to: nuclear size distributions and nuclear density on the mucosal surface and/or indentifying areas suspicious for dysplasia, in accordance with aspects of the invention.

Figure 13:
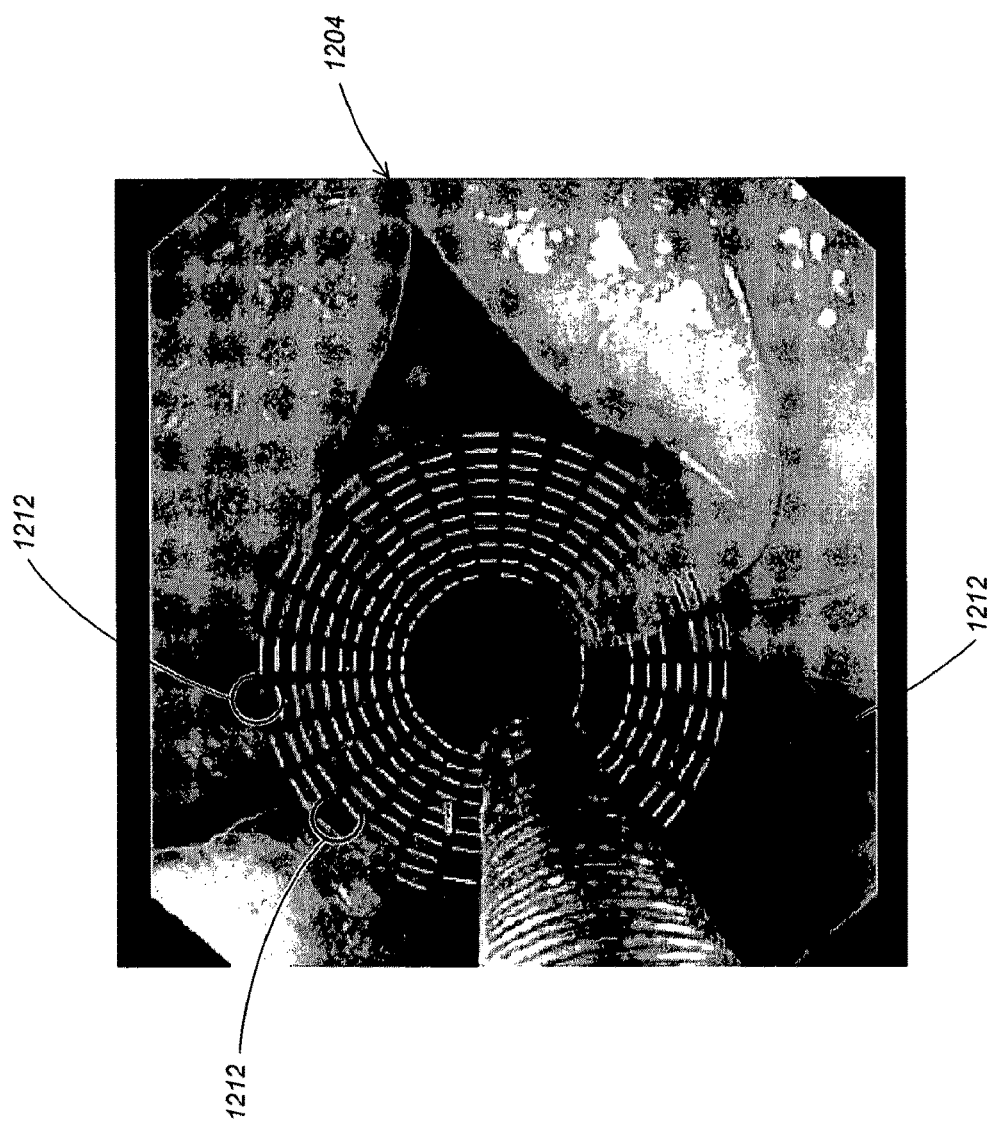
FIG. 13 illustrates a user interface having parameters, which are extracted from data using a histographic algorithm relating tissue structure and or a tissue condition to LSS data, and that are presented in the form of pseudocolor maps overlaid on a video image of Barrett's esophagus (BE)

The left panel 1202 shows the visual image of the esophagus acquired over a standard video input of the endoscope. The middle panel 1204 shows same image overlaid with a semitransparent color-coded map 1208 representing LSS derived diagnostic information. In FIG. 13, which shows an enlarged image of the middle panel 1204, where green spots (appearing light colored and unlabeled) represent the non-dysplastic areas and red spots, three of which are circled and labeled as 1212, represent the areas which are suspicious for dysplasia. Thus, sites suspicious for dysplasia may be identified. The bottom left panel 1214 shows the diffuse spectrum collected from one particular spot with white dots 1215 representing the experimental data and a solid (red) curve 1216 representing the model fit. The bottom right panel 1218 of the PLSS endoscopic scanning instrument interface window is also capable of displaying the residual of the parallel and perpendicular polarization spectra. These residual spectra represent a single scattering part of the signal and are diagnostically significant.

The histological algorithm described above may be used to convert the sum and the residual of the parallel and perpendicular polarization spectra into histological properties of the illuminated spot. The residual spectra are mainly originated in the epithelium and are analyzed to yield (1) epithelial nuclear size, (2) nuclear size distribution and (3) increase in chromatin density, thereby providing information about nuclear enlargement, crowding and hyperchromaticity. As described above, to extract nuclear size distributions, Applicants developed an algorithm that treats the experimentally observed LSS spectrum as a sum of the LSS spectra of cells nuclei and smaller individual organelles within the scanning spot of the instrument. The sum of two polarizations provides the diffuse reflectance spectrum yielding information about (4) the density of the collagen matrix, (5) hemoglobin concentration and (6) oxygen saturation of hemoglobin in the underlying tissue.

Histological/Biochemical Algorithm

Applicants have developed a histological algorithm that converts the detected LSS signal into the histological properties of the illuminated spot. The backscattering spectra which contain the diagnostic information can be extracted and analyzed to yield (1) epithelial nuclear size, (2) nuclear size distribution and (3) increase in chromatin density, thereby providing information about nuclear enlargement, crowding and hyperchromaticity. In addition, diffuse reflectance spectra can be been analyzed to yield information about (4) the density of the collagen matrix, (5) hemoglobin concentration and (6) oxygen saturation of hemoglobin in the underlying tissue. Applicants have also developed a diagnostic algorithm that translates these histological properties into diagnostic information. This algorithm may be implemented in as computer executable code for data analysis that executes on a computer associated with the EPSS system, on a different computer or computing device or on a remote server system, as the invention is not limited in this respect.

The information may be presented in the form of maps color-coded for probable diagnoses. These maps may be presented to the physician in real time, independently and/or overlaid on the visual images of the esophagus, and may be used to guide biopsies.

For rapid extraction of histological and biochemical tissue parameters, Applicants developed an inverse algorithm based on least-squares minimization. Because there can be multiple minima, biologically relevant intervals need to determined for each of the model parameters, and the intervals used as constraints in the minimization procedure to improve data extraction. In addition, Applicants have employed methods which deal with multiple minima (such as simulated annealing), and select the most suitable. Applicants' algorithm was tested on phantoms and then used in clinical data analysis.

Using the polarization technique described above, spectra of the parallel component $I_{\parallel}(\lambda)$ and perpendicular component $I_{\perp}(\lambda)$ at each point on the BE surface were measured. The residual of the parallel and perpendicular components $I_{LSS}(\lambda)=I_{\parallel}(\lambda)-I_{\perp}(\lambda)$ was processed using the LSS algorithm, and the sum of those components $I_{DRS}(\lambda)=I_{\parallel}(\lambda)+I_{\perp}(\lambda)$ was processed using the diffuse reflectance spectroscopy algorithm.

Applicants have shown that spectroscopic features of light backscattered from the epithelium can be used to extract important information about the stage and progression of dysplasia. Although nuclear size distributions are correlated with HGD, LDG and NGD in exemplary embodiment described herein, nuclear size distributions and nuclear densities may be correlated with other pathological diagnoses, and diagnostic thresholds may be defined for various tissue conditions as well as for various stages of precancerous conditions, as the invention is not limited in this respect.

The experimentally measured LSS spectrum is a linear combination of the LSS spectra of epithelial cell nuclei and other subcellular organelles of various sizes and refractive indices. The experimental residual spectrum $I_{LSS}(\lambda)$ can be expressed as an integral over the organelles' diameters δ and relative refractive index n, $$I_{LSS}(\lambda) = C(\lambda) \int_0^{\delta_{mas}} d\delta \int_{n_{min}}^{n_{max}} S(\lambda, \delta, n) F(\delta, n) \, dn + \varepsilon(\lambda), \quad (5)$$

where $S(\lambda, \delta, n)$ is the LSS spectrum of a single scatterer with diameter δ (within the range from 0 to $\delta_{max}$) and refractive index n (within the range from $n_{min}$ to $n_{max}$, $F(\delta, n)$ is the organelle size and refractive index distribution, and $\epsilon(\lambda)$ is the experimental noise. Applicants' goal was to determine that part of distribution $F(\delta, n)$ which describes the cell nuclei. The calibration function, $C(\lambda)$, takes into account characteristics of the instrument. It should be noted that because of light collimation, $C(\lambda)$ is independent of the distance to the target, and thus precise positioning of the optical head relative to the esophageal walls may not be needed. Equation (5) can be written as a discreet sum over organelles' diameters and refractive indexes:

$$I_K = C_k \sum_{i=1}^{N} \sum_{j=1}^{M(i)} F_{ij} \cdot S_{ij} + E_k, \quad (6)$$

where $F_{ij}$ is a discreet two-dimensional distribution, $$S_{ijk} = \int_{\delta_i}^{\delta_{i+1}} d\delta \int_{n_j(i)}^{n_{j+1}(i)} S(\lambda_k, \delta, n) \, dn,$$

noise $E_k$ is the sum of the experimental noise, errors associated with inaccuracy of the model, and discrimination errors, N is the number of discreet sizes, M(i) is the number of refractive indices for the sizes i, and $\lambda_k$ are discreet points across the spectral range, where k is changing from 1 to p. The number of unknowns in Eq. (6) is determined by the range of the diameters $\delta_R$ to $\delta_{max}$ and the range of refractive indices $n_{min}$ to $n_{max}$, and is equal to $$q = \sum_{i=1}^{N} M(i).$$

Since a certain amount of noise $E_k$ is present, it is not feasible to calculate the distribution $F_{ij}$ by directly inverting the matrix $S_{ijk}$. Therefore in order to solve equation (6) the following function may be minimized:

$$\Phi = \sum_{k=1}^{p} w_k \left( I_k - C_k \sum_{i=1}^{N} \sum_{j=1}^{M(i)} F_{ij} S_{ijk} \right)^2 \quad (7)$$

where $w_k$ is a weight function determined from noise analysis, and the sum is calculated over all spectral points. Minimizing $\Phi$ requires inverting the ill-conditioned matrix $$A_{nm} = \sum_{k=1}^{p} w_k \sum_{i=1}^{N} \sum_{j=1}^{M(i)} S_{ijk} S_{nmk}.$$

Thus, additional prior information about the distribution function $F_{ij}$ may be employed such as that the distribution function cannot be negative $F_{ij} \geq 0$. This is an important constraint, which makes the solution of problem (7) stable. The linear least squares with non-negativity constraints algorithm is used to invert the size and refractive index distribution.

By increasing the number of elements q in distribution $F_{ij}$, the discreet representation of $F_{ij}$ may be made more accurate. However, at the same time the condition number of the matrix $A_{nm}$ is significantly increasing with the increase of q, making the problem more unstable. Thus, q needs to be optimized. To do so, the amount of information present in the light scattering spectra should be evaluated.

The spectroscopic range of an exemplary system is from 400 nm to 800 nm with a resolution of 2 nm. This constitutes a bandwidth of 400 nm for p=200 independent spectral points. Thus, the highest number of points across the range of sizes and refractive indices q should be limited by 200. Since the Mie scattering calculations showed that: (1) the LSS spectra of small scatterers (smaller than 1 μm) are predominantly smooth, and (2) the shape of the LSS spectra of small scatterers is almost independent of the refractive index, the number of points needed to describe the contribution of the small particles is significantly smaller than p. Calculations show that 20 points is enough to describe the contribution of submicron organelles in epithelial cells. Because the nuclear size distribution is relatively smooth, approximately 15 points can be used to describe the size distribution of large particles (from 1 μm to 10 μm), which includes nuclei. Unlike spectra of the small particles, LSS spectra of the large particles are affected by the refractive index and 4 points are used to describe variation of the refractive indexes. The rest of the points in the distribution can be reserved to describe the shape of the nuclei, which initially is described by their elongation.

In experiments with mixtures of subcellular organelles of various sizes, Applicants tested some ideas described above. Applicants were able to accurately and consistently reconstruct the organelle size distributions and verify those distributions with electron microscopy. Using a similar approach, Applicants also reconstructed the nuclear size distribution in cell monolayers. Some significant improvements of this approach include (1) taking into account polarization of light, (2) describing the shape of the nuclei and (3) speeding up the analysis to be able to guide biopsy in real time.

In addition, as discussed above, Applicants developed a quantitative model of diffuse reflectance and applied it to the analysis of clinical reflectance spectra of BE.

Endoscopic Procedure with EPSS Instrument

Figure 15A:
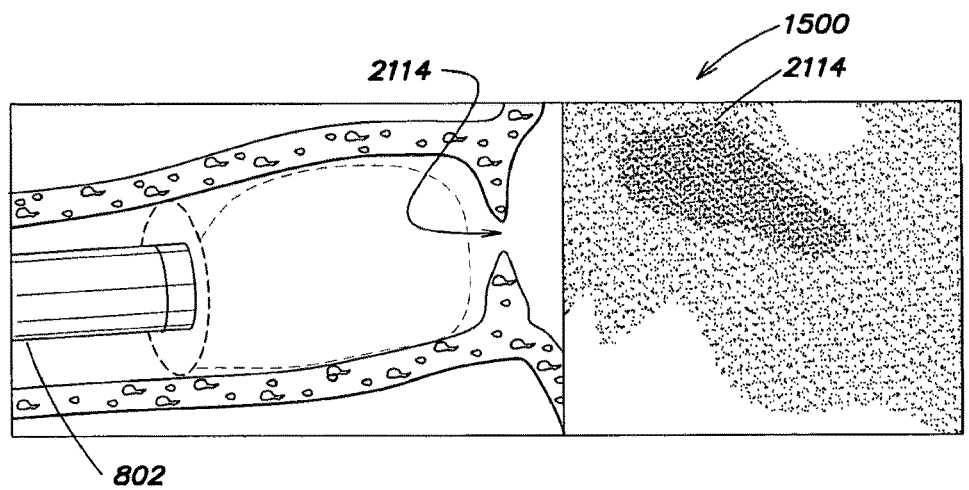
FIG. 15A schematically depicts an endoscope in the esophagus near the lower esophageal sphincter (LES) and a corresponding simulated view through the endoscope.
Figure 16:
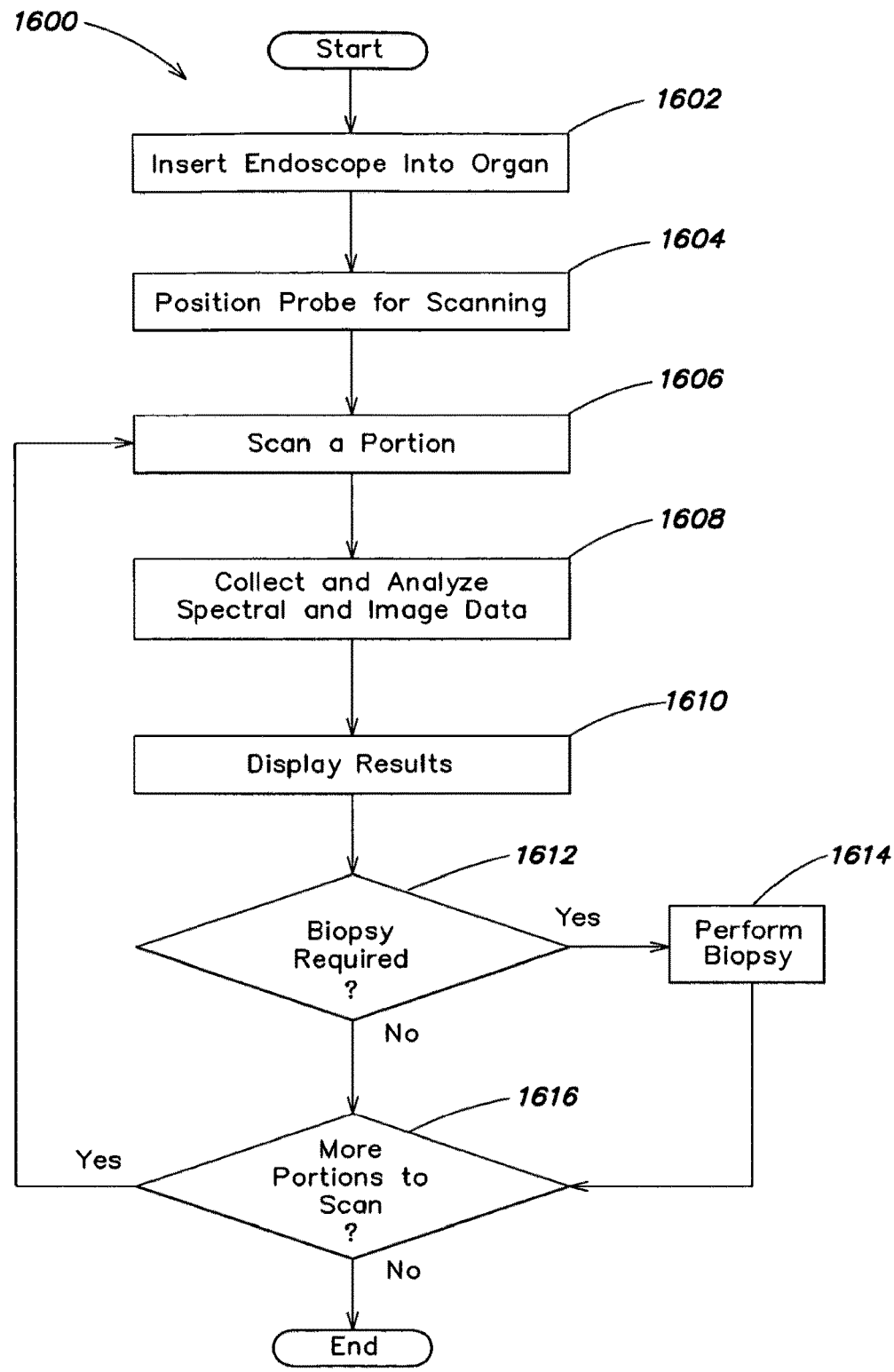
FIG. 16 is a flowchart illustrating an endoscopic procedure using of a EPSS instrument, in accordance with some embodiments of the invention.

In one embodiment, a EPSS system may work with commercially available gastroscopes. An exemplary measurement procedure 1600, which is shown as a flowchart in FIG. 16, is as follows:

Step 1. Insert Endoscope. The endoscope (e.g., gastroscope 802) may be inserted, in block 1602, into an organ such as the esophagus until it is about 2 cm from the lower esophageal sphincter (LES) 2114, as shown in FIG. 15A. The edge of the field of view may be about 2 cm from the LES 2114. The endoscope's view of the LES 1514 is shown on the simulated video monitor 1500 in FIG. 15A.

Figure 14A:
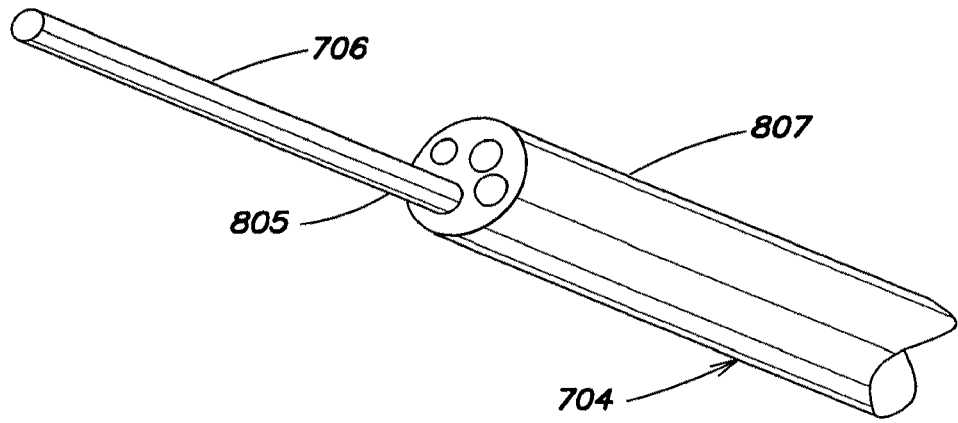
FIG. 14A illustrates a perspective view of a probe inserted through an instrument channel of a gastroscope (scope) with a tip of the probe extending approximately 2 cm from a distal end of the scope.
Figure 14B:
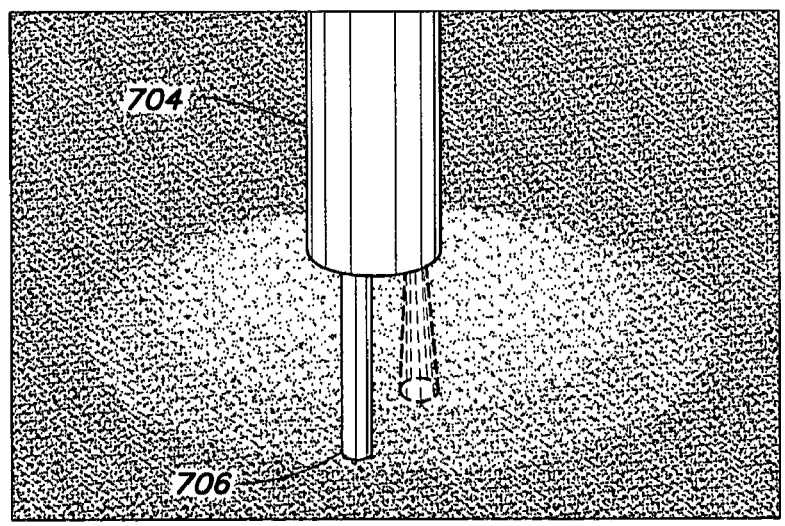
FIG. 14B illustrates the probe of FIG. 14A forming a 2 mm diameter spot on a flat surface.
Figure 15B:
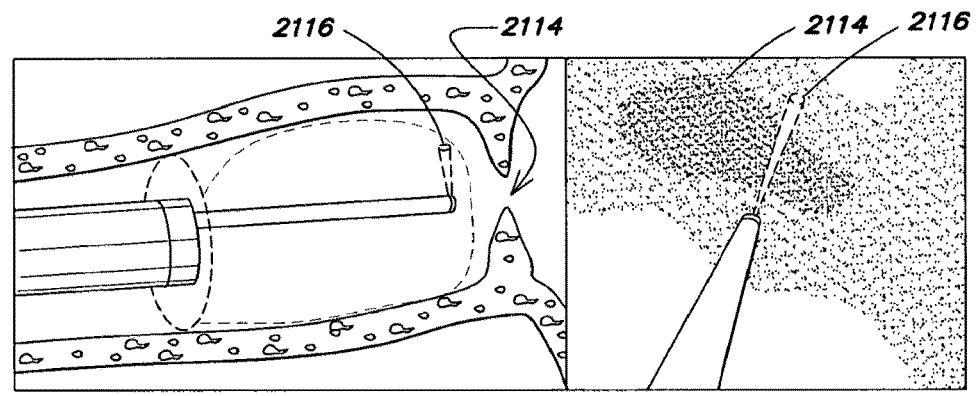
FIG. 15B schematically depicts a probe of the endoscope depicted in FIG. 15A advanced to a starting location of a scan and a corresponding simulated view through the endoscope where a white cone illustrates illumination by a light beam of the probe.

Step 2. Advance probe. At block 1604, the probe's light source may be turned on and the probe 706 may be positioned—i.e., advanced through the endoscope's instrument channel 805 until it is close to the LES (FIG. 15B), extending no more than 2.5 cm from the endoscope tip as shown in FIG. 14. The starting location of the spot 1516 is seen in the endoscope's video image 1500, as depicted in FIG. 15B. The spot has a nominal diameter of 2 mm. While looking at the video images, the endoscopist may articulate the tip of the scope slightly to insure that the probe is fairly centered in the esophagus.

Figure 15C:
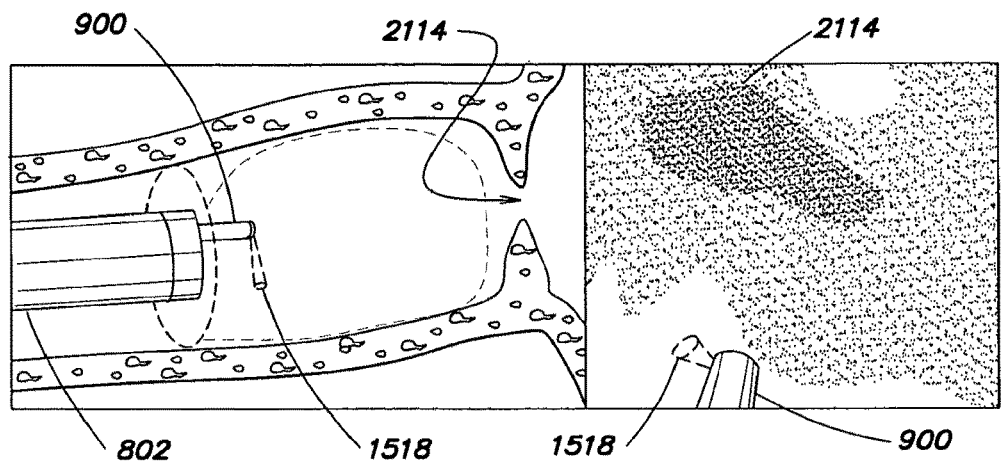
FIG. 15C schematically depicts a location of a beam of the probe at completion of the scan and a corresponding simulated view through the endoscope.

Step 3. Scan. When the starting location is correct, the scanning sequence is initiated, at block 1606. The LSS scanning may progress from the gastro-esophageal junction to the mouth. No biopsies are taken on the scan. The "flying spot" automatically indexes around the esophagus circumferentially in 30 angular increments to make one 360 degree sweep. The probe 706 may then be automatically moved proximally by 2 mm, and the angular sweep is repeated. This step and repeat process continues until a 2 cm wide band has been scanned (total time—20 sec.). The position 1518 of the flying spot at the end of the scan is shown in FIG. 15C.

Step 4. Data capture and documentation of suspicious sites. At each scanned location, spectral data is captured by two spectrometers, as shown in block 1608 of FIG. 16. Furthermore, as discussed above, one or more images (e.g., video images) of each scanner location, or a site, may be collected. At block 1620, the results may then be displayed. For example, distilled results of the spectral scan may be shown on the computer monitor in real time as the scan progresses, in the form of a false-color map overlaid, or superimposed, on a video image of Barrett's esophagus (FIG. 13). The diagnostic algorithm has been developed to work in real time and to alert a user such as an endoscopist or other medical practitioner when spectra indicating BE or dysplasia are found. Thus, the user may be provided with an indication of whether to obtain a tissue sample from an examined site.

Figure 15D:
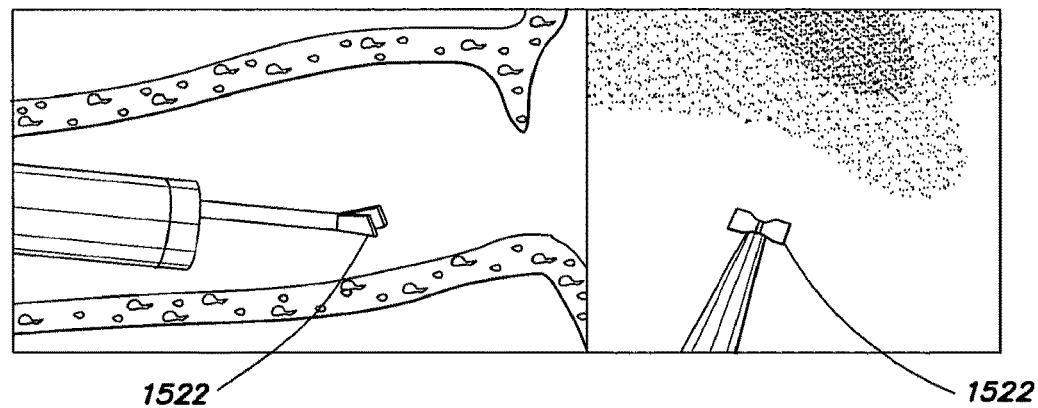
FIG. 15D schematically depicts a forceps biopsy guided by the optical probe and a corresponding simulated view through the endoscope.

Step 5. Forceps biopsy. At block 1612, it may be determined whether biopsy is required, based on analysis of the results displayed at block 1610. If it is determined that the biopsy is required, the process 1600 continues to block 1614, where, while observing the live image, as well as the stored image for reference, biopsy forceps 1522 may be advanced through the endoscope's second instrument channel 807 (see also FIG. 14A). The scope 802 may be articulated as needed to guide the forceps. In the locations suspicious for dysplasia as indicated by the instrument the endoscopist will collect forceps biopsies. FIG. 15D shows the forceps 1522 taking a biopsy and the view through the gastroscope 802. It should be appreciated that even though, in FIG. 16, blocks 1606-1618 illustrate respective steps of process 1600 in certain order, the steps may be performed in any suitable order and one or more of the steps may be performed simultaneously. Thus, as discussed above, displaying the results at block 1610 may be performed simultaneously with performing biopsy at block 1614.

When it is determined, at block 1612, that the biopsy is not required, process 1600 may continue to block 1616 where it may be determined whether more portions of the esophagus need to be scanned. If it is determined that more portions of the esophagus need to be scanned, process 1600 may return to block 1606 to scan more portions, as discussed above. The determination may be performed automatically or in any other suitable manner.

Step 6. Move proximally, repeat. If it is determined, at block 1616, that the endoscopist wishes to scan more of the esophagus, the endoscope is pulled back proximally in 2 cm increments and the scanning process is repeated, from block 1606.

In some embodiments, standard endoscopic Narrow Band Imaging (NBI) may be employed in combination with the Polarized LSS Endoscopic Scanning Instrument to allow data collection simultaneously with the noninterrupted visual observation of the gastrointestinal tract. In addition, as discussed above, embodiments of the invention are not limited to detection of abnormal changes in organs of gastrointestinal tract and may be applied to various organs of reproductive tract, respiratory tract and other systems.

It should be appreciated that the above processing described in connection with FIG. 16 is exemplary only and similar technique may be used to detect abnormal morphological and biochemical changes in various others organs of gastrointestinal, reproductive, respiratory and other tracts. Moreover, scanning of internal and external surfaces of the organs may be performed, in accordance with some embodiments of the invention.

Multispectral Scanning During Endoscopy for Guiding Biopsy

As discussed above, Applicants have demonstrated that the EPSS system provided by some embodiments of the invention is suitable for use in a clinical setting. Described below are some results of endoscopy experiments performed by Applicants on freshly resected bovine esophagi and in humans. The experiments were performed using a system such as one shown in FIGS. 7-12, with particular exemplary setting as described below. Furthermore, during the endoscopy, images of the examined tissue and collected information were displayed on a display device comprising a user interface similar to the one shown in FIG. 13.

In one experiment, performance of the EPSS system instrument was assessed using freshly resected bovine esophagi. An endoscope was inserted into a vertically mounted bovine esophagus which was then scanned point-by-point and resulting data was recorded. Histological specimens were taken at the EPSS data collection sites. Comparing nuclear sizes revealed by the H&E image (i.e., the image generated from a sample stained using hematoxylin and eosin stain, as known in the art) with the EPSS result, showed reasonable agreement, as shown in FIGS. 17A and 17B.

Figure 17A:
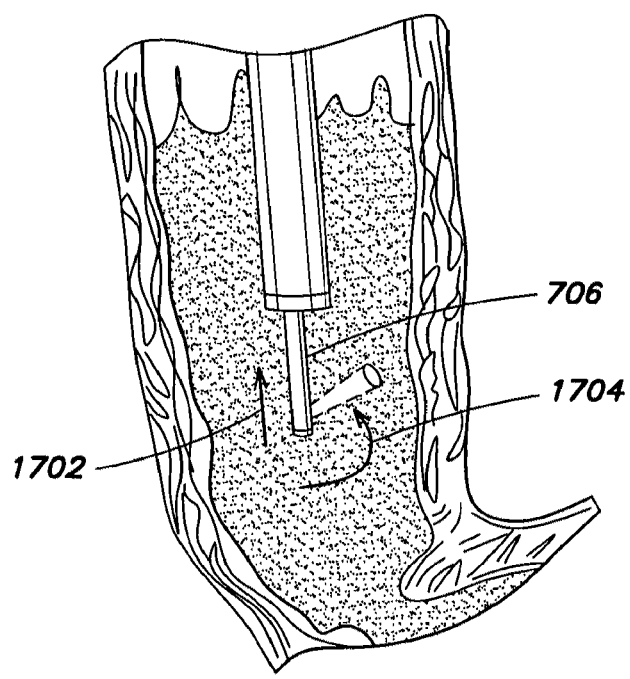
FIGS. 17A and 17B illustrate results of EPSS scanning of esophageal epithelium during screening endoscopy, n accordance with one embodiment of the invention.
Figure 17B:
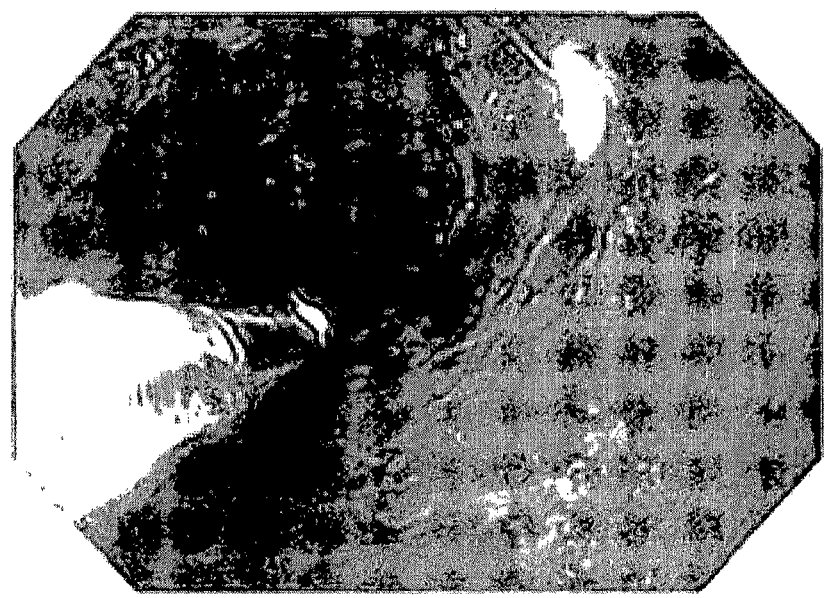

FIGS. 17A and 17B illustrate EPSS scanning of esophageal epithelium during screening endoscopy. In particular, FIG. 17A illustrates a tip of probe 706 (e.g., probe 900) extended from working channel of the endoscope 704 during scan; arrows 1702 and 1704 indicate linear (1702) and rotary (1704) motions of probe tip before and during each scan, respectively. FIG. 17B illustrates frame capture, obtained and displayed via the EPSS user interface, of an image acquired by the endoscope video channel showing the actual EPSS probe tip during scanning of the esophageal epithelium of a patient with Barrett's esophagus during a clinical procedure. The scanning illumination spot 1706 may be seen on the esophagus wall at the upper right of the image. In this example, the EPSS probe tip diameter is 2.5 mm.

In another experiment, Applicants performed clinical measurements using the EPSS system during endoscopic procedures for individuals with suspected dysplasia who had consented to participate in the study, at the (IEC) Beth Israel Deaconess Medical Center (BIDMC) Interventional Endoscopy Center. Subjects reporting to the IEC at BIDMC underwent initial screening at other institutions and were referred with confirmed Barrett's esophagus and suspicion of dysplasia. The procedure, indications, preparation and potential complications were explained to the subjects, who indicated their understanding and signed the corresponding consent forms. Applicants' protocol was reviewed by the BIDMC Institutional Review Board and the requisite approvals obtained.

In this experiment, Applicants employed a high resolution endoscope (HRE) with Narrow Band Imaging (NBI) such as, for example, an Olympus GIF-H180 gastroscope manufactured by the Olympus America, Inc. A gastroenterologist introduced the gastroscope, which had an EPSS polarized fiber optic probe in the working channel, through the mouth. The EPSS performed optical scanning of each complete, continuous region of the luminal esophageal wall chosen for examination by the gastroenterologist. Data obtained from the optical scans for each linear and angular position of the probe tip as parallel and perpendicular polarization reflectance spectra, corrected for light source intensity and lineshape, was recorded.

The following algorithm was used to distinguish non-dysplastic Barrett's esophagus from sites of HGD and LGD. The backscattering spectrum at each individual spatial location, m, was extracted by subtracting perpendicular from parallel polarized reflectance spectra, $S_m^{BS}(\lambda) = S_m^{\parallel}(\lambda) - S_m^{\perp}(\lambda)$. The backscattering spectra were then normalized to remove amplitude variations due to peristalsis, $$S_m(\lambda) = \frac{S_m^{BS}(\lambda)}{\sqrt{\sum_\lambda S_m^{BS}(\lambda)^2}} \quad (8)$$

where $S_m(\lambda)$ is the normalized spectrum and the summation is performed over all spectral points $\lambda$. The root mean square normalized spectrum was calculated as follows, $$\overline{S}(\lambda) = \sqrt{\frac{1}{N} \sum_{m=1}^{N} S_m(\lambda)^2} \quad (9)$$

where N is the total number of scanned positions. For each measurement site m, the difference of the normalized spectrum $S_m(\lambda)$ from the root mean square normalized spectrum $\overline{S}(\lambda)$, was calculated, squared and summed over all spectral points to obtain a diagnostic parameter $\Delta_m$ at each site $$\Delta_m = \frac{1}{2} \sum_\lambda (S_m(\lambda) - \overline{S}(\lambda))^2 \quad (10)$$

If this diagnostic parameter was greater than 0.1 (which is 10% of the mean squared spectrum summed over all spectral points) the site was considered to be dysplastic. In this example, the calibration was not performed.

The above analysis is straightforward and may therefore be performed in near real time. By extracting the nuclear size distributions from the backscattering spectra for each individual spatial location, Applicants have found that this is approximately equivalent to a contribution of more than 25% from enlarged nuclei over 9 microns in diameter. The pseudo-color maps based on this rule were then drawn and shown to the physician in each case where the EPSS instrument was used to guide the biopsy.

For the longitudinal coordinate, the starting position was measured by the distance from the upper incisors. The probe is then retracted in 2 mm steps. The starting position of the azimuthal coordinate is observable by the bright spot on the esophagus and then the data is collected every 12°. For guiding biopsy upon return examination, these coordinates are provided to the gastroenterologist. Also, the esophagus has many landmarks, which may be observable under NBI. For every map location the gastroenterologist is provided with a freeze frame image which can be used to aid in locating the guided biopsy spot using these landmarks. The same freeze frame image shows the EPSS illuminated spot where the spectrum was acquired. The EPSS spot in relation to the landmarks is used to reduce the potential problems due to peristaltic motion. Using the longitudinal and azimuthal coordinates of an EPSS mapped site, along with the associated landmarks and freeze frame image showing the illuminated spot on the esophageal wall, it may be estimated the gastroenterologist may return to the same spot within a 5 mm radius upon a subsequent examination. However, it should be noted that the follow up case presented in this example may not exemplify the intended application of the instrument in accordance with some embodiments of the invention. In practice, biopsies would be performed as dysplastic sites are first identified and mapped by EPSS, during the same procedure and not in a follow-up procedure. Hence biopsies would be guided in the initial exam, in the sense that EPSS would identify a dysplastic site where a confirmative biopsy should be perfoinied, rather than performing biopsies in a predetermined, "blind" pattern.

Figure 18A:
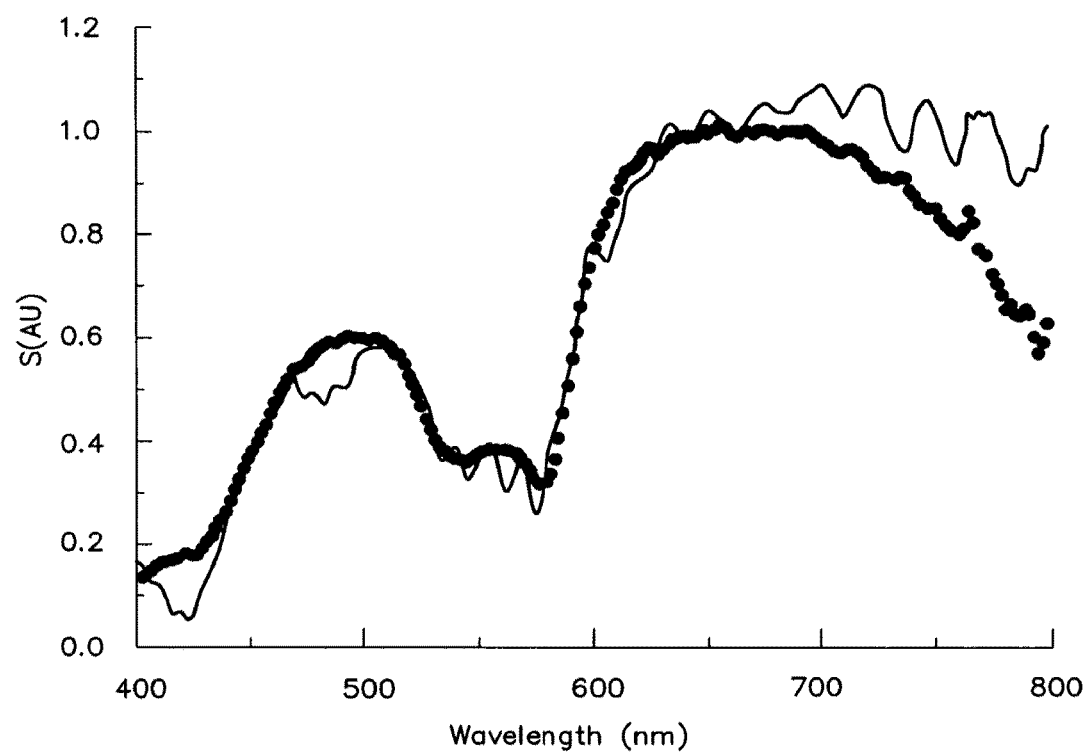
FIGS. 18A and 18B illustrate spectra acquired during routine screening endoscopy, in accordance with one embodiment of the invention.

Two observations may support the clinical feasibility of the above method. First, spectroscopic data collected during clinical procedures confirm that the polarization technique may be very effective in removing unwanted background signals. For example the perpendicular polarization spectral component, originating in the deeper tissue layers, exhibits standard diffuse reflectance features, with hemoglobin absorption bands clearly observable in the 540-580 nm region. The parallel polarization spectral component, in addition to diffuse features, exhibits a very clear oscillatory structure, characteristic of diagnostically important nuclear scattering originating in the uppermost epithelial layer, as shown in FIG. 18A. This figure illustrates parallel (solid line) and perpendicular (dotted line) polarization spectra collected with the EPSS instrument from a single spatial location in a subject with Barrett's esophagus.

Figure 18B:
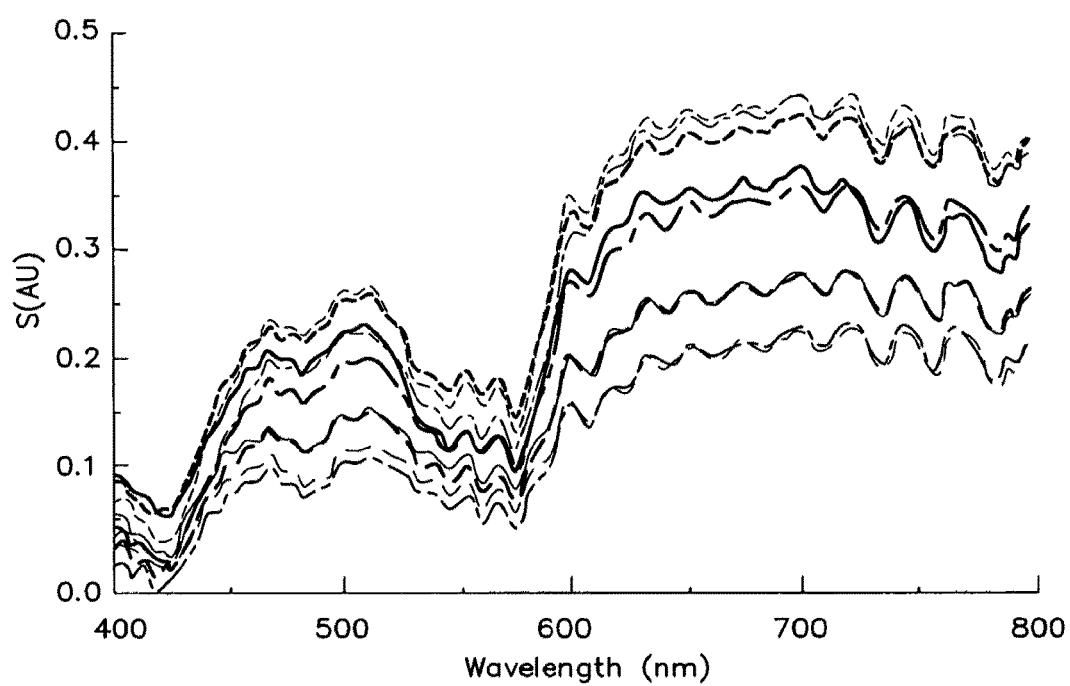

Second, the issue of peristaltic motion may be addressed by EPSS. During a procedure, it is difficult to maintain a fixed distance between the optical probe head and the esophageal surface, due to peristaltic motion and other factors. Therefore, an important feature of the EPSS instrument may be its ability to collect spectra of epithelial tissue that are not affected by the orientation or distance of the distal probe tip to the mucosal surface. This may be achieved with collimated illumination and collection optics. Thus, a probe may be positioned at a distance within a range of distances from an examined site. Analysis of parallel polarization spectra collected at ten different locations from the same subject during a standard clinical procedure (FIG. 18B) showed that although amplitudes of the spectra differ from site to site, the spectral shape is practically unchanged. The fluctuation of the normalized difference of the perpendicular and parallel spectra in the 600 to 800 nm spectral range which carries the diagnostic information is substantially less than 10% for non-dysplastic sites, regardless of the distance of the probe from the esophageal wall.

Applicants have collected a total of 10,800 EPSS spectra in eight procedures, covering the entire scanned regions of the esophagus in seven subjects. Further, Applicants have validated the capabilities of the method by comparing EPSS data with subsequent pathology at each site where biopsies were taken. For the first two subjects, pathology was reported per quadrant not per biopsy, and so the data was not used.

Figure 19A:
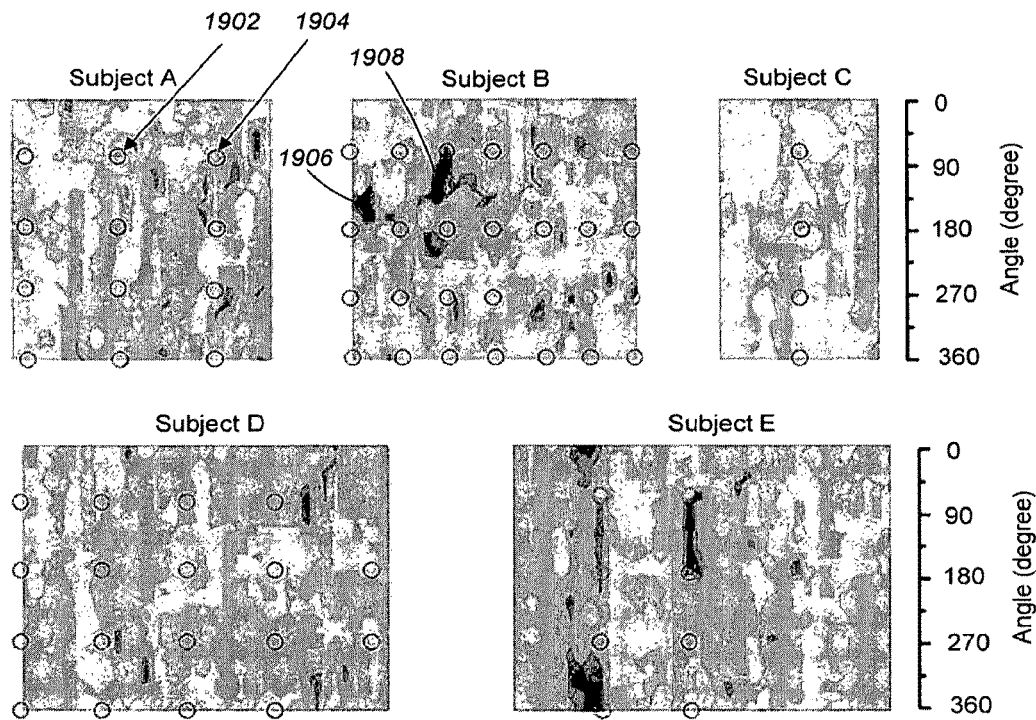
FIG. 19A illustrates EPSS maps comprising biopsy sites and pathology for subjects A through E, in accordance with one embodiment of the invention.
Figure 19B:
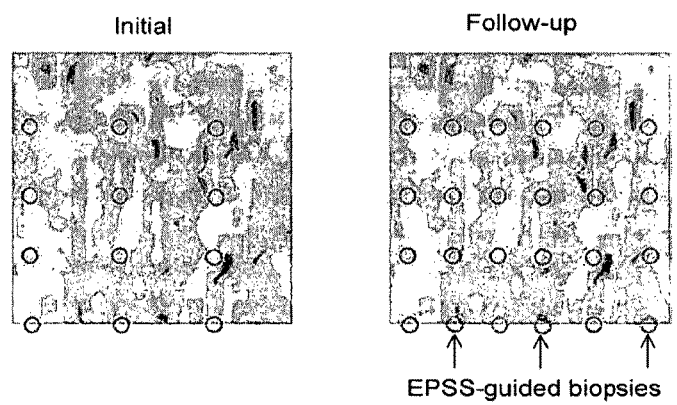
FIG. 19B illustrates biopsies taken during the initial and follow-up endoscopy procedures for subject A, overlaid on the EPSS map acquired during the initial procedure, in accordance with one embodiment of the invention.

For the other subjects, 95 biopsies were collected according to the standard-of-care. The locations of biopsied tissue sites were recorded by their distances from the upper incisors and their angles relative to the start of the EPSS scan (FIGS. 19A and 19B). Pathological examination revealed a total of 13 dysplastic sites of which 9 were HGD and 4 were low grade to dysplasia (LGD). The rest of the sites were diagnosed as non-dysplastic.

FIGS. 19A and 19B illustrate visual representations, or maps, produced from EPSS data that are overlaid with circles indicating biopsy sites and confirmed pathology. For illustration purposes only, two circles, 1902 and 1904, indicating respective biopsy sites, are marked in FIG. 19A. Vertical axis indicates angle of rotation in degrees from start of each rotary scan; horizontal axis indicates distance in cm from upper incisors. In FIG. 19A, exemplary map areas colored with different shades of grey are shown. The maps may be presented to a user in a color format. Accordingly, in FIG. 19A, different shades of grey, from the lightest to the darkest, may represent blue-, green-, pink- and red-colored areas of the map, respectively. Blue and green map areas represent epithelium that is unlikely affected by dysplasia; red and pink map areas represent epithelium that is suspicious for dysplasia, as determined by EPSS. Two of the map areas colored in red are marked as 1906 and 1908.

Further, in FIG. 19A, highlighted solid, dashed and solid without highlighting circles indicate biopsy sites of HGD, LGD and non-dysplastic Barrett's esophagus, respectively, as determined by pathology. FIG. 19A illustrates EPSS maps comprising biopsy sites and pathology for subjects A through E. FIG. 19B illustrates biopsies taken during the initial and follow-up endoscopy procedures for subject A, overlaid on the EPSS map acquired during the initial procedure. Three follow-up biopsies were guided by the EPSS map and pathology confirmed HGD for each (indicated at 360°).

The diagnoses for each EPSS location were extracted from the residuals of the parallel and perpendicular backscattered spectral components collected by the EPSS instrument. The results may be presented as pseudo-color maps, as shown in FIG. 19A.

Double blind comparison of the EPSS maps with the biopsy reports revealed 11 true positive sites, 3 false positive sites, 80 true negative sites, and 1 false negative site (FIG. 19A). Thus, in this example, EPSS measurements are characterized by sensitivity of 92% and specificity of 96%.

Figure 20:
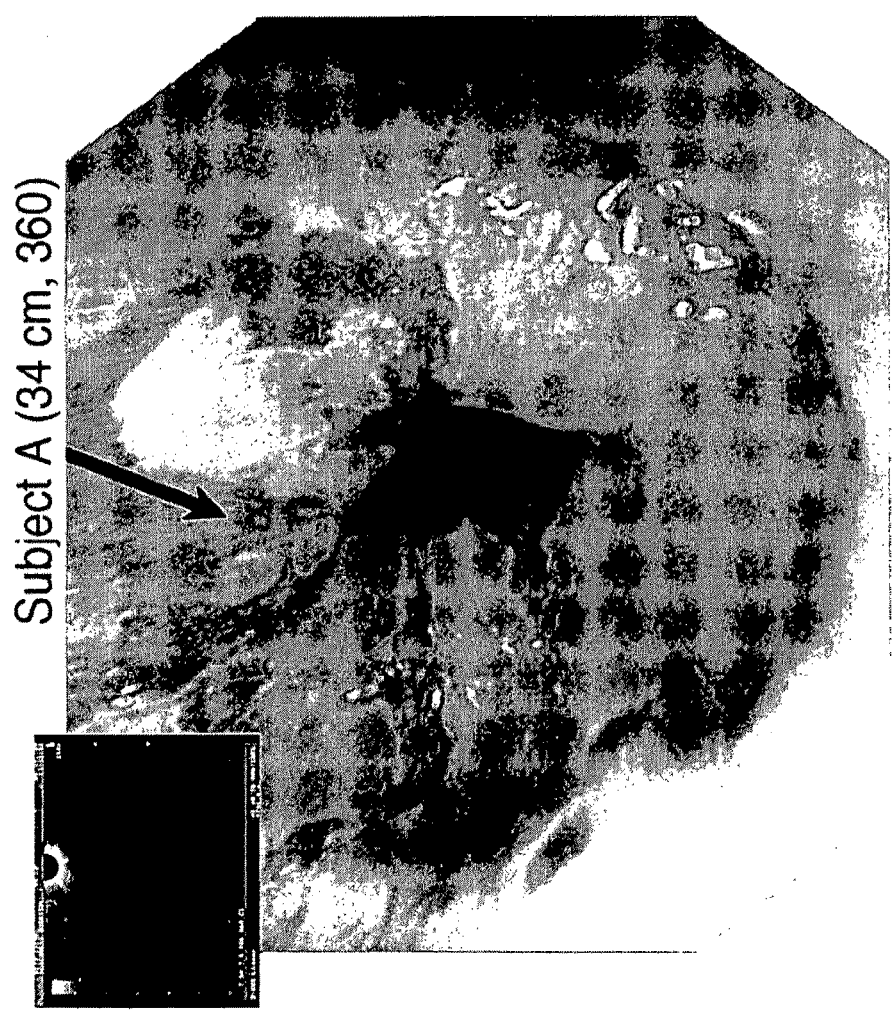
FIG. 20 illustrates an image of a location with invisible high-grade dysplasia (HGD) obtained using a high resolution endoscope (HRE) with Narrow Band Imaging (NBI), in accordance with one embodiment of the invention.

The third Barrett's esophagus subject (the first in whom individually marked biopsies were taken, subject A in FIG. 19A) underwent endoscopy and biopsy, concurrent with EPSS. Visual endoscopic examination using HRE with NBI did not reveal any areas suspicious for dysplasia. Pathology of tissue biopsies taken in the pattern prescribed by the standard-of-care revealed no dysplasia and the subject was dismissed. However, the EPSS scan indicated several probable sites of focal dysplasia, which were located in regions where biopsies were not taken. Hence, subject A was recalled and several biopsies were taken in the vicinity of each site indicated by EPSS plus a repeat of the standard-of-care protocol. Video capture was acquired in subject A at one of the locations where invisible dysplasia was missed by visual examination by HRE with NBI but located by EPSS and confirmed later by pathology. As shown in FIG. 20, a freeze frame of the endoscopic video image of a site identified by EPSS as suspicious for dysplasia demonstrates that the site is visually indistinguishable from the surrounding non-dysplastic tissue even under HRE with NBI. This site is marked by an arrow 2000 in FIG. 20.

Pathology confirmed HGD at all three EPSS directed sites and one additional HGD at a point located between two EPSS indicated sites (FIG. 19B). The latter site, considered a false negative, is very close to the sites indicated by EPSS and may arise from imperfect correspondence of actual biopsy site with EPSS mapped site. This subject will now be given appropriate treatment. Standard-of-care procedures, even when diligently performed by highly skilled and experienced gastroenterologists, can miss focal dysplasias because these procedures biopsy only a very small fraction of esophageal tissue, blindly according to the prescribed protocol. The capability of EPSS to examine the entire esophageal epithelium millimeter-by-millimeter enables detection of dysplastic cells and guidance of confiimative biopsy, greatly increasing the probability of early detection and treatment and in all likelihood, of saving lives.

Pathology found HGD in biopsies from subjects B and E, who need to be treated. No suspicious sites were found in subject C, as shown in FIG. 19A. However, EPSS found a number of suspicious sites in subject D, while standard-of-care biopsies located no abnormal pathology. Subject D may be recalled for further examination.

The frequency of dysplasia in the subject sample is consistent with that of the pre-screened population referred to the BIDMC IEC for confirmation and treatment but is higher than would be expected in the general Barrett's esophagus subject population. In fact, the frequency of HGD detection in the general population of Barrett's esophagus subjects underscores the importance of having more comprehensive and effective methods for gastroesophageal cancer screening.

The Applicants' experiments described above demonstrated that the system employing a combination of endoscopy with polarized light scattering spectroscopy, in accordance with some embodiments of the invention, is well suited for use in clinical settings. The system employs imaging of an examined site of the tissue, where the resulting images are associated (e.g., overlaid with or otherwise combined) with maps (e.g., color-coded maps) representing structural characteristics of the tissue at the site. Thus, a user such as a medical practitioner may be presented with such mapping for diagnosis of suspicious sites. The user may be presented with the mapping, or other suitable representation of the results of the scanning, either during the scanning procedure itself (e.g., in "real time") or after the results have been collected and stored. When the results are presented to the user during the scanning procedure, as each site is being illuminated, imaged, and the resulting spectra of backscattered light are analyzed, the user may perform biopsy at the sites that are identified as suspicious. Accordingly, during the scanning, the biopsy may be guided—i.e., it may only be performed for sites that are identified as potentially exhibiting abnormal changes, which contrasts with performing biopsy in a predetermined pattern. As a result, burden on a patient may be alleviated.

In the system, the probe associated with the endoscopic instrument is rotatable and enables scanning of area of 360° of the examined organ such as the esophagus, used as an example organ throughout this description. The probe may be non-contact. Employing of such probe allows rapid scanning of the entire surface of the organ such as the esophagus.

It has been shown that the system may allow detecting sites suspicious for dysplasia that are undetectable using other existing methods. Indeed, the screening of several patients showed that a site that is detected as suspicious for dysplasia using the Applicants' system is visually indistinguishable from the surrounding non-dysplastic tissue even under HRE with NBI. This early detection of a potentially precancerous change in the tissue may improve a chance of a successful treatment of a respective patient.

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method steps, system element, instrument elements and/or probe elements, it should be understood that those acts and those elements may be combined in other ways to accomplish the same objectives. Acts, elements and features discussed only in connection with one embodiment are not intended to be excluded from a similar role in other embodiments.

What is claimed is:

1. Apparatus for obtaining characteristics of a surface of a hollow organ, the apparatus comprising:
    a probe configured to scan the surface of the hollow organ, the probe comprising:
        polarization and collimating optics configured to illuminate at least one portion of the hollow organ with polarized and collimated light having a first polarization, and
        light collection optics configured to receive light backscattered by the at least one portion as a result of the illumination;
    at least one spectrometer configured to generate at least one spectrum from the received light;
    an imager configured to capture at least one image of the at least one portion; and
    an analysis unit configured to analyze the at least one spectrum associated with the backscattered light to determine wavelength-dependent values of a reduced scattering coefficient for a sub-epithelial region of the at least one portion and to detect at least one abnormal morphological change of the at least one portion from the wavelength-dependent values.

2. The apparatus of claim 1, wherein the analysis unit is further configured to determine a correspondence between the at least one image and the at least one abnormal morphological change.

3. The system of claim 1, further comprising a user interface configured to present information comprising the at least one image in association with at least one visual representation of the at least one abnormal morphological change, wherein the information is used to determine whether to take a tissue sample from the at least one portion.

4. The apparatus of claim 3, wherein the information comprises the at least one image superimposed with the at least one visual representation of the at least one abnormal morphological change.

5. The apparatus of claim 3, wherein the information is presented as at least one of a color map and a pseudocolor map.

6. The apparatus of claim 1, wherein the at least one spectrum comprises a summation of backscattered light having a same polarization as the first polarization and backscattered light having a second polarization that is perpendicular to the first polarization.

7. The apparatus of claim 6, wherein the at least one abnormal morphological change comprises a degree of dysplasia of the at least one portion.

8. The apparatus of claim 6, wherein the analysis unit is configured to determine a degree of dysplasia of the at least one portion based, at least in part, upon the wavelength-dependent values of the reduced scattering coefficient.

9. The apparatus of claim 1, wherein the probe is configured to be located at a distance from the at least one portion without contacting a surface of the at least one portion.

10. The apparatus of claim 1, wherein the imager is configured to obtain the at least one image of the at least one portion at a time when the probe scans the at least one portion.

11. The apparatus of claim 1, wherein the wavelength-dependent values comprise multiple values of reduced scattering coefficients recorded at a same wavelength.

12. The apparatus of claim 1, wherein the wavelength-dependent values comprise slopes of wavelength-dependent reduced scattering coefficients.

13. The apparatus of claim 1, wherein at least some of the polarization and collimating optics are rotatable to scan the polarized and collimated light over the surface of the hollow organ.

14. The apparatus of claim 1, wherein at least some of polarization and collimating optics rotate with respect to a non-scanning portion of the probe or an instrument into which the probe is inserted.

15. The apparatus of claim 1, wherein the hollow organ comprises an esophagus.

16. The system of claim 1, wherein the analysis unit is further configured to analyze a difference of parallel and perpendicular polarization components of the received light to detect the at least one abnormal morphological change.

17. A method of spectral analysis of light reflected from a surface of an esophagus, the method comprising:
    obtaining, with an imager, at least one video image of at least one site of the surface of the esophagus;
    illuminating, with light from an optical probe, the at least one site with polarized and collimated light having a first polarization;
    processing reflected light from the at least one site to obtain at least one spectrum;
    analyzing, with a processor, the at least one spectrum to determine wavelength-dependent values of a reduced scattering coefficient for a sub-epithelial region of the at least one site;
    determining at least one indicator of at least one abnormal change at the at least one site from the wavelength-dependent values of the reduced scattering coefficient; and
    presenting a representation of the at least one video image in association with the at least one indicator.

18. The method of claim 17, wherein presenting the representation comprises:
    displaying the representation on a display to indicate whether to take a sample of tissue from the at least one site.

19. The method of claim 17, wherein presenting the representation comprises displaying the at least one video image superimposed with the at least one indicator.

20. The method of claim 17, wherein processing the reflected light comprises summing reflected light having a same polarization as the first polarization and reflected light have a second polarization that is perpendicular to the first polarization.

21. The method of claim 20, wherein the wavelength-dependent values comprise slopes of wavelength-dependent reduced scattering coefficients.

22. The method of claim 20, further comprising determining a characteristic from the at least one spectrum that is selected from the group consisting of: density of collagen matrix, concentration of hemoglobin and oxygen saturation of hemoglobin at the at least one site.

23. The method of claim 17, wherein the reflected light comprises reflected collimated light.

24. The method of claim 17, wherein the wavelength-dependent values comprise values of reduced scattering coefficients determined at a same wavelength.

25. The method of claim 24, further comprising determining a degree of dysplasia at the at least one site from the values of reduced scattering coefficients determined at the same wavelength.

26. An apparatus for obtaining characteristics of a surface of an esophagus, the apparatus comprising:
 an endoscope;
 an optical probe configured to be inserted into the endoscope, wherein the probe is moveable and rotatable with respect to the endoscope, the probe comprising:
  polarization and collimation optics configured to illuminate at least one portion of the esophagus with polarized collimated light having a first polarization, and
  light collection optics configured to receive light backscattered by the at least one portion as a result of the illumination;
 at least one spectrometer configured to generate at least one spectrum from the received light;
 an imager configured to capture at least one image of the at least one portion;
 an analysis unit configured to analyze the at least one spectrum to determine wavelength-dependent values of a reduced scattering coefficient for a sub-epithelial region of the at least one portion and to detect at least one abnormal morphological change of the at least one portion; and
 a user interface configured to present to a user information comprising the at least one image in association with at least one visual representation of the at least one abnormal morphological change.

27. The apparatus of claim 26, wherein the analysis unit is further configured to analyze a difference of parallel and perpendicular polarization components of the received light to detect the at least one abnormal morphological change.

* * * * *

UNITED STATES PATENT AND TRADEMARK OFFICE
CERTIFICATE OF CORRECTION

PATENT NO. : 9,788,728 B2
APPLICATION NO. : 13/145851
DATED : October 17, 2017
INVENTOR(S) : Lev T. Perelman It is certified that error appears in the above-identified patent and that said Letters Patent is hereby corrected as shown below:

In the Specification

At Column one, the RELATED APPLICATIONS section should read as follows:
This application is the National Stage of International Application No. PCT/US2010/000166, filed January 22, 2010, which claims the benefit under 35 U.S.C. § 119(e) of U.S. provisional application 61/147,074, filed January 23, 2009, entitled "POLARIZED LSS ENDOSCOPIC SCANNING INSTRUMENT," the content of which is incorporated herein in its entirety.

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*